(12) United States Patent
Emrich et al.

(10) Patent No.: US 7,981,606 B2
(45) Date of Patent: Jul. 19, 2011

(54) CONTROL FOR NUCLEIC ACID TESTING

(75) Inventors: Thomas Emrich, Iffeldorf (DE); Gerd Haberhausen, Penzberg (DE); Martin Moczko, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 559 days.

(21) Appl. No.: 11/638,655

(22) Filed: Dec. 12, 2006

(65) Prior Publication Data

US 2007/0141563 A1 Jun. 21, 2007

(51) Int. Cl.
*C12Q 1/68* (2006.01)
(52) U.S. Cl. ........ 435/6; 435/91.1; 435/91.2; 536/24.33
(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. | |
| 4,683,202 A | 7/1987 | Mullis | |
| 4,786,600 A | 11/1988 | Kramer et al. | |
| 4,876,187 A | 10/1989 | Duck et al. | |
| 4,996,143 A | 2/1991 | Heller et al. | |
| 5,011,769 A | 4/1991 | Duck et al. | |
| 5,118,801 A | 6/1992 | Lizardi et al. | |
| 5,130,238 A | 7/1992 | Malek et al. | |
| 5,185,243 A | 2/1993 | Ullman et al. | |
| 5,210,015 A | 5/1993 | Gelfand et al. | |
| 5,399,491 A | 3/1995 | Kacian et al. | |
| 5,403,711 A | 4/1995 | Walder et al. | |
| 5,409,818 A | 4/1995 | Davey et al. | |
| 5,455,166 A | 10/1995 | Walker | |
| 5,487,972 A | 1/1996 | Gelfand et al. | |
| 5,541,311 A | 7/1996 | Dahlberg et al. | |
| 5,565,322 A | 10/1996 | Heller | |
| 5,573,907 A | 11/1996 | Carrino et al. | |
| 5,614,402 A | 3/1997 | Dahlberg et al. | |
| 5,660,988 A | 8/1997 | Duck et al. | |
| 5,679,524 A | 10/1997 | Nikiforov et al. | |
| 5,705,365 A | 1/1998 | Ryder et al. | |
| 5,710,029 A | 1/1998 | Ryder et al. | |
| 5,719,028 A | 2/1998 | Dahlberg et al. | |
| 5,804,375 A | 9/1998 | Gelfand et al. | |
| 5,843,669 A | 12/1998 | Kaiser et al. | |
| 5,846,717 A | 12/1998 | Brow et al. | |
| 5,849,489 A | 12/1998 | Heller | |
| 5,888,779 A | 3/1999 | Kacian et al. | |
| 6,162,603 A | 12/2000 | Heller | |
| 6,174,670 B1 | 1/2001 | Wittwer et al. | |
| 6,277,560 B1 | 8/2001 | Andrieu et al. | |
| 2003/0077622 A1 | 4/2003 | WalkerPeach et al. | |
| 2005/0227229 A1* | 10/2005 | Lebo et al. ................. | 435/6 |

FOREIGN PATENT DOCUMENTS

| | | |
|---|---|---|
| EP | 0 200 362 B1 | 10/1986 |
| EP | 0 201 184 B1 | 12/1986 |
| EP | 0 320 308 B1 | 6/1989 |
| EP | 0 329 822 B1 | 8/1989 |
| EP | 0 389 063 B1 | 9/1990 |
| EP | 0 439 182 B1 | 7/1991 |
| EP | 1 236 805 A1 | 9/2002 |
| EP | 1 319 716 A1 | 6/2003 |
| WO | WO 89/09835 A1 | 10/1989 |
| WO | WO 89/12696 A1 | 12/1989 |
| WO | WO 90/01069 A1 | 2/1990 |
| WO | WO 92/02638 A1 | 2/1992 |
| WO | WO 92/08808 A1 | 5/1992 |
| WO | WO 95/05480 A1 | 2/1995 |
| WO | WO 95/14106 A1 | 5/1995 |
| WO | WO 97/46707 A1 | 12/1997 |
| WO | WO 97/46712 A1 | 12/1997 |
| WO | WO 97/46714 A1 | 12/1997 |
| WO | WO 99/06594 A1 | 2/1999 |
| WO | WO 99/16781 A1 | 4/1999 |
| WO | WO 01/37291 A1 | 5/2001 |
| WO | WO 02/18635 A2 | 3/2002 |
| WO | WO 2004/055205 A2 | 7/2004 |
| WO | WO 2004/104229 A2 | 12/2004 |
| WO | WO 2005/016737 A1 | 2/2005 |
| WO | WO 2005/061737 A1 | 7/2005 |

OTHER PUBLICATIONS

EP 05028004.9 Search Report, Roche Diagnostics GmbH, Jun. 19, 2006.
EP2005/001243 Search Report, Roche Diagnostics GmBH, Mar. 27, 2007.
Abramson, R., et al., 1993, "Nucleic acid amplification technologies", *Analytical Biotechnology*, 4:41-47.
Ausubel, F., et al., 2001, "Current Protocols in Molecular Biology", vols. 1, 2, 3 and 4.
Barany, F., 1991, "The Ligase Chain Reaction in a PCR World", *PCR Methods and Applications*, 1:5-16.
Barany, F., 1991, "Genetic disease detection and DNA amplification using cloned thermostable ligase", *PNAS*, 88:189-193.
Beaucage, S., et al., 1981, "Deoxynucleoside Phosphoramidites—A New Class of Key Intermediates for Deoxypolynucleotide Synthesis", *Tetrahedron Letters*, 22(20):1859-1862.
Bernard, P, et al., 1998, "Integrated Amplification and Detection of C677T Point Mutation in the Methyleneterrahydrofolate Reductase Gene by Fluorescence Resonance Energy Transfer and Probe Melting Curve", *Analytical Biochemistry*, 255 : 101-107.

(Continued)

*Primary Examiner* — Heather Calamita
(74) *Attorney, Agent, or Firm* — Charles M. Doyle; Olga Kay

(57) ABSTRACT

The present invention is related to a method for detecting a target biomolecule in test sample by adding an internal control biomolecule to the test sample; to a negative control sample, to a positive control sample and to a reagent control sample or adding an internal control biomolecule to the test sample, to a negative control sample, to a positive control sample comprising the target biomolecule and providing a reagent control sample comprising the target biomolecule, determining in each sample a signal, and verifying the signal thereby detecting the target biomolecule. The invention is also related to a method for verifying the determination of a signal indicating the presence of a target biomolecule. The invention is further related to a method for detecting the presence or the absence of a member of a group of target nucleic acids in a sample and a method for verifying the determination of a signal indicating the presence of a member of a group of target nucleic acids.

15 Claims, 5 Drawing Sheets

OTHER PUBLICATIONS

Brakenhoff, R., et al., 1999, "Sensitive Detection of Squamous Cells in Bone Morrow and Blood of Head and Neck Cancer Patients by E48 Reverse Transcriptase-Polymerase Chain Reaction", *Clinical Cancer Research*, 5: 725-732.

Brown, E., et al., 1979, "Chemical Synthesis and Cloning of A Tyrosine tRNA Gene", *Methods in Enzymology*, 68 (8):109-151.

Chelly, J., et al. 1990, Quantitative estimation of minor mRNAs by CDNA-polymerase chain reaction. Application to dystrophin mRNA in cultured myogenic and brain cells, *'Eur J. of Biochem*, 187:691-698.

Clementi, M., et al., 1993, "Quantitative PCR and RT-PCR in Virology", *PCR Methods and Applications*: 2: 191-196.

Clementi, M., et al., 1995, "Quantitative Molecular Methods in Virology", *Arch Virol*, 140: 1523-1539.

Gait, MJ, 1984"Oligonucleotide Synthesis, A practical Approach", IRL Press Limited, Oxford England.

Garegg, P., et al., 1985, "Formation of Internucleotidic Bonds via Phosphonate Intermediates", *Chemica Scripta*, 25:280-282.

Gilliland, G., et al., 1990, "Analysis of cytokine mRNA and DNA: Detection and Quantitation by competitive polymerase chain reaction", *PNAS*, 87:2725-2729.

Gilliland, G., et al., 1990, Isothermal, in vitro amplification of nucleic acids by a multienzyme reaction modeled after retroviral replication' , *PNAS*, 87:1874-1878.

Haentjens-Herwegh, S., et al., 2000, "Development and Use of Internal Positive Controls for PCR Detection of Microorganisms", *Recent Res. Devel. Microbiology*, 4: 547-556.

Hamed, B., et al., 1985, "Nucleic Acid Hybridisation", IRL Press Limited, Oxford England.

Kwoh, D., 1989, "Transcription-based amplification system and detection of amplified human immunodeficiency virus type 1 with a bead-based sandwich hybridization format", *Proc. Natl. Acad. Sci USA*, 86:1173-1177.

Leushner, J., 2000, Detection of Pathogenic enteric bacteria in stool by multiplex PCR, Qiagen News, www.qiagen.com.

Mallet, F., et al., 1995, Quantitation of Human Immunodeficiency Virus Type 1 DNA by two PCR Procedures coupled with enzyme-linked oligosorbent assay, *Journal of Clinical Microbiology*, 33 (12) 3201-3208.

Minerva Biolaps, 2004, Legionella species Detection Kit for Conventional PCR.

Narang, S., et al., 1979, "Improved Phosphotriester Method for the Synthesis of Gene Fragments", *Methods in Enzymology*, 68(6):90-98.

Roche Diagnostics—COBAS AMPLICOR™ CT/NG Test for Chlamydia trachomatis, Instruction Manual.

Roche Diagnostics—LightCycler® foodproof *E.coli*0157 Detection Kit, Instruction Manual.

Sambrook, J., et al., 1989, "Molecular Cloning A Laboratory Manual", *CSH*, $2^{nd}$ Edition.

Takara Bio Inc., 2004, CycleavePCR™ Meat Species Identification Kit, Cat # CY204, http://www.takara-bio.co.jp.

Valentine-Thon, E., 2002, Review: Quality Control in Nucleic Acid Testing—where so we stand?', *Journal of Clinical Virology*, 25:513-521.

Whelen, A., et al., 1996, "The Role of Nucleic Acid Amplification and Detection in the Clinical Microbiology Laboratory", *Annu. Rev. Microbiol.*, 50:349-373.

Wittwer C., et al., 1997, Continuous Fluorescence Monitoring of Rapid Cycle DNA Amplification, *BioTechniques*, 22:130-138.

Wu, D., et al., 1989, "The Ligation Amplification Reaction (LAR)—Amplification of Specific DNA Sequences Using Sequential Rounds of Template-Dependent Ligation", *Genomics*, 4:560-569.

\* cited by examiner

US 7,981,606 B2

CONTROL FOR NUCLEIC ACID TESTING

This application claims the benefit of priority under 35 U.S.C. §119 of EP Application 05028004.9, filed Dec. 21, 2005, the contents of which are hereby incorporated by reference.

BACKGROUND OF THE INVENTION

1. Field of the Invention

The present invention is related to a method for detecting a target biomolecule in a test sample by adding an internal control biomolecule to the test sample; to a negative control sample, to a positive control sample and to a reagent control sample or adding an internal control biomolecule to the test sample, to a negative control sample, to a positive control sample comprising the target biomolecule and providing a reagent control sample comprising the target biomolecule, determining in each sample a signal, and verifying the signal thereby detecting the target biomolecule. The invention is also related to a method for verifying the determination of a signal indicating the presence of a target biomolecule. The invention is further related to a method for detecting the presence or the absence of a member of a group of target nucleic acids in a sample and a method for verifying the determination of a signal indicating the presence of a member of a group of target nucleic acids. Uses and kits are considered as well.

2. Description of Related Art

The determination of nucleic acids has become an important tool in analytical chemistry, especially in health care. For example, infection diseases and genetic status can be easily determined on the basis of the presence or the amount of a nucleic acid indicative of said disease or status in samples received from the individual. For this reason methods were established using sequence specific hybridization of a nucleic acid, preferably an oligonucleotide, with a target nucleic acid indicative for that disease or genetic status. Many target nucleic acids are present in an organism in such low concentration, that a direct detection in a sample derived from that organism is not possible. Such targets need to be amplified before detection. Suitable amplification methods are for example LCR (U.S. Pat. Nos. 5,185,243, 5,679,524 and 5,573,907; EP 0 320 308; WO 90/01069; WO 89/12696; and WO 89/09835), cycling probe technology (U.S. Pat. Nos. 5,011,769, 5,403,711, 5,660,988, and 4,876,187, and PCT published applications WO 95/05480, WO 95/14106, and WO 95/00667), Invader™ technology (U.S. Pat. Nos. 5,846, 717; 5,614,402; 5,719,028; 5,541,311; and 5,843,669), Q-Beta replicase technology (U.S. Pat. No. 4,786,600), NASBA (U.S. Pat. No. 5,409,818; EP-0 329 822), TMA (U.S. Pat. Nos. 5,399,491, 5,888,779, 5,705,365, 5,710,029), SDA (U.S. Pat. Nos. 5,455,166 and 5,130,238) and PCR (U.S. Pat. No. 4,683,202).

In order to minimize false results in nucleic acid determinations, authorities in several countries require the use of control nucleic acids. Especially when using amplification methods such control nucleic acids are very important, because the amplification process can be strongly influenced by the reaction conditions, which could lead to misleading results. Sometimes inhibitory substances are contained in a sample, which could lead to false negative results. A review of control concepts is provided by Valentine-Thon, E., J. Clinical Virol. 25 (2002) S13-S21.

In general one can distinguish external and internal controls. External controls, like classical positive and negative controls, mimic positive and negative samples and are normally used to check whether the assay runs properly or whether contaminants are contained. An internal control for example is useful for recognizing inhibitory substances possibly contained in a sample or can be used as a quantification standard in a quantitative assay. In contrast to an external control, which normally is tested in a separate reaction chamber, an internal control is preferably incubated in the same reaction chamber together with the analyte to be tested. Therefore, the control or the amplified product of that control has to be distinguishable from the analyte or from the amplified product of that analyte. When using an amplification method an internal control nucleic acid is being co-amplified essentially under the same reaction conditions as the target nucleic acid. These conditions include reagent concentrations, temperature, inhibitor concentration or enzymatic activities. Frequently used sequences for controls are derived from housekeeping genes (see Chelly, J., et al., Eur. J. Biochem. 187 (1990) 691-698; Mallet, F., et al., J. Clin. Microbiol. 33 (1995) 3201-3208), but also non-natural sequences are being used (see e.g. EP 1 236 805).

The amplified nucleic acid derived from the internal control can be distinguished from the amplified nucleic acid derived from the target nucleic acid for example by their different length or hybridization capability to a distinct probe (for reviews see: Clementi, M., et al., PCR Methods Applic. 2 (1993) 191-196; Clementi, M., et al., Arch. Virol. 140 (1995) 1523-1539). In all cases the nucleotide sequence of the internal control is partially or totally different from the target nucleic acid sequence (see also Haentjens-Herwegh, S., et al., Recent Res. Devel. Microbiology 4 (2000) 547-556).

One of the most critical aspects in an amplification reaction is the binding of the primer to the target nucleic acid. Therefore internal controls are being used, which have the same primer binding sites as the target nucleic acid (see for example Gilliland, G., et al., Proc. Natl. Acad. Sci. USA 87 (1990) 2725-2729).

WO 02/18635 and WO 99/06594 disclose the use of encapsulated internal control sequences mimicking nucleic acids encapsulated in a virus shell.

EP 1 319 716 discloses the use of several discriminable internal control nucleic acids for testing nucleic acid isolation and amplification.

WO 2004/055205 discloses the addition of internal control sequences to a sample which undergoes sample preparation. Then the signal from the IC is compared to external controls which did not undergo sample preparation in order to verify the efficiency of cell lysis and of sample preparation as well as the performance of nucleic acid amplification and/or detection.

U.S. Pat. No. 6,277,560 discloses the use of the DNA of an external microorganism as external standard for quantification and the use of an internal control for evaluating the efficiency of nucleic acid amplification.

Gilliland, G., et al., Proc. Natl. Acad. Sci. USA 87 (1990) 2725-2729 discloses the use of negative controls and internal controls for quantification.

Brakenhoff, R., et al., Clin. Cancer Res. 5 (1999) 725-732 disclose a PCR assay with an internal standard for RNA quality control, an external standard for sensitivity control and a negative control. WO 2005/061737 discloses a kit with an internal control, a positive control and a negative control.

Leushner and Kelly, Qiagennews, No. 4, 2000, page 21, disclose a method for detection of pathogenic enteric bacteris in stool by multiplex PCR using an internal control and a positive control.

The "LightCycler® foodproof *E. coli* 0157 Detection Kit" manufactured by Roche Applied Sciences (Mannheim, Germany) discloses in its manual a PCR method for the qualitative detection of *E. coli* serotype 0157 using an internal control and a control template.

US2003/077622 relates to methods and compositions that provide a positive control to identify inhibition during a signal amplification reaction.

The "CT/NG Test for *Chlamydia trachomatis*" manufactured by Roche Molecular Systems (Branchburg, N.J., USA) discloses in its manual a PCR method for detection of *Chlamydia trachomatis* using an internal control and the *C. trachomatis* target DNA.

The manual for the CycleavePCR™ meat species identification kit manufactured by TaKaRa, Japan, discloses a method for the differentiation of different meat species including a control concept.

SUMMARY OF THE INVENTION

It was an object of the invention to provide new concepts for controlling methods for the detection of biomolecules.

In an embodiment of the invention, a method is provided for detecting the presence or the absence of a target biomolecule in a sample suspected to comprise the target biomolecule comprising:
  a) either
    a1) adding an internal control biomolecule
      to the sample suspected to comprise the target biomolecule,
      to a negative control sample not comprising the target biomolecule,
      to a positive control sample comprising the target biomolecule, and
      to a reagent control sample comprising the target biomolecule; or
    a2) adding an internal control biomolecule
      to the sample suspected to comprise the target biomolecule,
      to a negative control sample not comprising the target biomolecule, and
      to a positive control sample comprising the target biomolecule, and providing a reagent control sample comprising the target biomolecule,
  b) optionally purifying the biomolecules from the samples of step a) to obtain samples comprising the purified biomolecules,
  c) determining in each sample obtained in step a) or b) the presence or the absence of a signal of the internal control biomolecule and of the target biomolecule,
  d) verifying the presence or absence of the signal of the target biomolecule in the sample suspected to comprise the target biomolecule by:
    checking the sample suspected to comprise the target biomolecule for the presence of a signal for the target biomolecule independently from the presence of a signal of the internal control biomolecule or checking for the presence of a signal of the internal control biomolecule in the case of an absence of a signal for the target biomolecule,
    checking the negative control sample for the presence of a signal of the internal control biomolecule and for the absence of a signal of the target biomolecule,
    checking the positive control sample for the presence of a signal of the target biomolecule and for the presence of a signal of the internal control biomolecule, and
    checking the reagent control sample for the presence of a signal for the target biomolecule in step d) of the method or checking the reagent control sample for the presence of a signal for the target biomolecule and optionally for the internal control biomolecule,
  e) detecting the presence or the absence of the target biomolecule whereby the presence or absence of the signals for the target biomolecule and the internal control biomolecule determined in step c) and verified in step d) indicate the presence or the absence of the target biomolecule in the test sample.

In another embodiment of the invention, a method for verifying the determination of a signal indicating the presence of a target biomolecule comprising:
  a) providing
    a sample suspected to comprise the target biomolecule and comprising an internal control biomolecule, and
    a negative control sample comprising an internal control biomolecule and not comprising the target biomolecule, and
    a positive control sample comprising the target biomolecule and comprising an internal control biomolecule
    a reagent control sample comprising the target biomolecule and optionally comprising an internal control biomolecule,
  b) determining in each sample the signal of the internal control biomolecule and of the target biomolecule,
  c) verifying the presence of the signal of the target biomolecule in the test sample indicating the presence of the target biomolecule in the test sample by:
    checking the sample suspected to comprise the target biomolecule for the presence of a signal for the target biomolecule independently from the presence of a signal of the internal control biomolecule or checking for the presence of a signal of the internal control biomolecule in the case of an absence of a signal for the target biomolecule,
    checking the negative control sample for the presence of a signal of the internal control biomolecule and for the absence of a signal of the target biomolecule,
    checking the positive control sample for the presence of a signal of the target biomolecule and for the presence of a signal of the internal control biomolecule, and
    checking the reagent control sample for the presence of a signal for the target biomolecule and optionally for the internal control biomolecule.

In still another embodiment of the invention, a method for detecting the presence or the-absence of a member (or target nucleic acid) of a group of target nucleic acids in a sample suspected to comprise the member of a group of target nucleic acids by:
  a) adding an internal control nucleic acid
    to the sample suspected to comprise a member (or target nucleic acid) of the group of target nucleic acids, and
    to a negative control sample not comprising a member member (or target nucleic acid) of the group of target nucleic acids, and
    to a positive control sample comprising a member member (or target nucleic acid) of the group of target nucleic acids,
  b) providing a reagent control sample comprising the group of target nucleic acids and optionally an internal control nucleic acid,
  c) optionally purifying the nucleic acids from the samples of step a) and/or b) to obtain samples comprising the purified nucleic acids,
  d) determining in each sample obtained in the steps a) and b) or in the steps b) and c) the presence or absence of a signal of the internal control nucleic acid and of a signal of a member (or target nucleic acid) of the group of target nucleic acids, e) verifying the presence or the absence of the signal of the member (or target nucleic acid) of the group of target nucleic acids in the sample suspected to comprise a member (or target nucleic acid) of the group of target nucleic acids by:

checking the sample suspected to comprise a member (or target nucleic acid) of the group of target nucleic acids for the presence of a signal of a member (or target nucleic acid) of the group of target nucleic acids independently from the presence of a signal of the internal control nucleic acid or checking for the presence of a signal of the internal control nucleic acid in the case of an absence of a signal of a member (or target nucleic acid) of the group of target nucleic acids, checking the negative control sample for the presence of a signal of the internal control nucleic acid and for the absence of a signal of the target nucleic acid, checking the reagent control sample for the presence of a signal of each member (or target nucleic acid) of the group of target nucleic acids and optionally of the internal control nucleic acid, and checking the positive control sample for the presence of a signal of a member (or target nucleic acid) of the group of target nucleic acids and for the presence of a signal of the internal control nucleic acid or, f) detecting the presence or the absence of a member (or target nucleic acid) of the group of target nucleic acids whereby the presence and/or the absence of the signals for a member (or target nucleic acid) of the group of target nucleic acids and the internal control nucleic acid determined in step d) and verified in step e) indicate the presence or the absence of a member (or target nucleic acid) of the group of target nucleic acids in the sample suspected to comprise a member (or target nucleic acid) of the group of target nucleic acids.

Throughout the application, the terms member of a group of target nucleic acids or target nucleic acid of a group of target nucleic acids or selected from a group of target nucleic acids are used interchangeably.

In yet another embodiment of the invention, a method for verifying the determination of a signal indicating the presence of a member of a group of target nucleic acids is provided comprising the steps of a) providing a sample suspected to comprise a member of the group of target nucleic acids and comprising an internal control nucleic acid, a reagent control sample comprising the group of target nucleic acids and optionally an internal control nucleic acid, a negative control sample not comprising a member of the group of target nucleic acids and comprising an internal control nucleic acid, and a positive control sample comprising a member of the group of target nucleic acids and an internal control nucleic acid, b) determining in each sample the signal of the internal control nucleic acid and of a member of the group of target nucleic acids, c) verifying the presence of the signal of a member of the group of target nucleic acids in the sample suspected to comprise a member of the group of target nucleic acids by:

checking the sample suspected to comprise a member of the group of target nucleic acids for the presence of a signal of a member of the target nucleic acids independently from the presence of a signal of the internal control nucleic acid or checking the sample for the presence of a signal of the internal control nucleic acid in the case of an absence of a signal of a member of the group of target nucleic acids, checking the reagent control sample for the presence of a signal of each member of the group of target nucleic acids, checking the negative control sample for the absence of a signal of a member of the group of target nucleic acids and for the presence of a signal of the internal control nucleic acid, and checking the positive control sample for the presence of a signal of the target biomolecule and for the presence of a signal of the internal control nucleic acid.

In another embodiment of the invention, a reagent control sample optionally comprising an internal control biomolecule and a positive control sample comprising an internal control biomolecule, both samples comprising the target biomolecule, are used for detecting the presence or the absence of a target biomolecule in a sample suspected to comprise the target biomolecule or for verifying the determination of a signal indicating the presence of a target biomolecule.

In another embodiment, a kit is provided for the detection of a target nucleic acid or a member of a group of target nucleic acids comprising a) a reagent control sample comprising the target nucleic acid or the member of a group of target nucleic acids, b) a negative control sample not comprising the target nucleic acid or the member of a group of target nucleic acids, c) a positive control sample comprising the target nucleic acid or the member of the group of target nucleic acids, d) an internal control nucleic acid, and e) reagents for detecting the target nucleic acid or the member of a group of target nucleic acids.

As is known in the art, a "nucleoside" is a base-sugar combination. The base portion of the nucleoside is normally a heterocyclic base. The two most common classes of such heterocyclic bases are the purines and the pyrimidines, in more detail the adenine (A), guanine (G), thymine (T) or cytosine (C) base. The uracil base is naturally contained in the ribonucleic acid. Another naturally occurring base is 5-methyl-cytosine or methyl-cytosine, which is cytosine which is substituted by a methyl group at the 5-position of the aromatic ring of the base. The sugar portion is normally a pentofuranosyl sugar, e.g., a ribose or deoxyribose.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression therefor is deoxyribonucleic acid (DNA) and ribonucleic acid (RNA).

A "nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined. Therefore, in other words the "nucleic acid" is the target and can therefore be also denoted as "target nucleic acid". For example, if it has to be determined whether blood contains the human immunodeficiency virus, the "target nucleic acid" is the nucleic acid of the human immunodeficiency virus or more specifically the nucleic acid sequence, i.e. the order of the bases adenine, guanine, cytosine, uracil, or thymine, that is determined. More specifically in the context of the invention, the "target nucleic acid" is preferably a nucleic acid or more precisely or preferably a part of the of the nucleic acid contained in a microorganism, cell or virus ("target microorganism", "target cell" or "target virus") as further specified herein. The "target nucleic acid" has a nucleic acid sequence specific for the microorganism, cell or virus and is part of the (total) nucleic acid contained in a microorganism, cell or virus.

According to the invention, an "oligomeric compound" is a compound consisting of "monomeric units" which may be "nucleotides" alone or "non-natural compounds", more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of a "oligomeric compound" or "polymeric compound" of ribonucleic acid (RNA) or deoxyribonucleic acid (DNA) with "monomeric units". The phosphate groups are commonly referred to as forming the internucleoside backbone of the "oligonucleotide". The normal linkage or backbone of RNA and DNA is a 3' to 5' phosphodiester linkage.

"Oligonucleotides" and "modified oligonucleotides" according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang, S. A., et al., Methods Enzymol. 68 (1979) 90-98, the phosphodiester method disclosed by Brown, E. L., et al., Methods Enzymol. 68 (1979) 109-151, the phosphoramidite method disclosed in Beaucage, S. L., and Caruthers, M. H., Tetrahedron Lett. 22 (1981) 1859-1862, the H-phosphonate method disclosed in Garegg, P. J., et al., Chem. Scr. 25 (1985) 280-282 and the solid support method disclosed in U.S. Pat. No. 4,458,066.

As said above, a "nucleic acid" as well as the "target nucleic acid" is a polymeric compound of "nucleotides" as known to the expert skilled in the art. It is used herein to denote a "nucleic acid" in a sample which should be analyzed, i.e. the presence, non-presence or amount thereof in a sample should be determined.

The term "primer" is used herein as known to the expert skilled in the art and refers to "oligomeric compounds" primarily to "oligonucleotides" but also to "modified oligonucleotides" that are able to "prime" DNA synthesis by a template-dependent DNA polymerase, i.e. the 3'-end of the e.g. oligonucleotide provides a free 3'—OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except for the intended function—no fundamental difference in nucleotide sequence between a "primer", an "oligonucleotide" or a "probe" according to the invention.

The term "probe" refers to synthetically or biologically produced nucleic acids (DNA or RNA) which, by design or selection, contain specific nucleotide sequences that allow them to hybridize under defined predetermined stringencies specifically (i.e., preferentially) to "target nucleic acids". A "probe" can be identified as a "capture probe" meaning that it "captures" the target nucleic acid so that it can be separated from undesirable materials which might obscure its detection. Once separation is accomplished, detection of the captured "target nucleic acid" can be achieved using a suitable procedure. "Capture probes" are often already attached to a solid phase. A specific example therefor is the microarray situation wherein a multitude of "capture probes" are attached to a "solid phase" which "capture" labeled cRNA or cDNA. In another aspect, a "probe" is an oligonucleotide that bears a detectable label.

"Labels", often referred to as "reporter groups", are generally groups that make a nucleic acid, in particular the "oligomeric compound" or the "modified oligonucleotide" according to the invention, as well as any nucleic acids bound thereto distinguishable from the remainder of the liquid, i.e. the sample (nucleic acids having attached a "label" can also be termed labeled nucleic acid binding compounds, labeled probes or just probes).

Haptens (such as biotin or digoxigenin), enzymes (such as alkaline phosphatase or peroxidase) or fluorescent dyes (such as fluorescein or rhodamine) have, among others, mainly proven to be suitable as non-radioactive indicator molecules or in other words as non-radioactive "labels". These "signal groups" or "labels" can be attached to or incorporated in nucleic acids by various methods. Preferred "labels" according to the invention are dyes as a fluorescein dye, a rhodamine dye, a cyanine dye, and a coumarin dye or haptens as biotin. By general definition, a "hapten" is a small molecule which is not by itself an immunogen (can cause an immune response), but has at least one element of an antigen and can combine with an antibody or another larger carrier molecule to become immunogenic.

As used herein, "fluorescence resonance energy transfer relationship" and similar terms refer to adjacent hybridization of an "oligomeric compound" labeled with a "donor fluorescent label" and another "oligomeric compound" labeled with an "acceptor fluorescent label" to a "target nucleic acid" such that the "donor fluorescent label" can transfer resonance energy to the "acceptor fluorescent label" such that the "acceptor fluorescent label" produces a measurable fluorescence emission. If the "donor fluorescent label" and "acceptor fluorescent label" are spaced apart by too great a distance, then the "donor fluorescent label" cannot transfer resonance energy to the "acceptor fluorescent label" such that the "acceptor fluorescent label" emits measurable fluorescence, and hence the "donor fluorescent label" and "acceptor fluorescent label" are not in resonance energy transfer relationship.

In the context of this invention, "hybridization" shall mean hydrogen bonding, which may be Watson-Crick, Hoogsteen or reversed Hoogsteen hydrogen bonding, between complementary nucleotides of separate oligonucleotides. For example, adenine and thymine are complementary nucleobases which pair through the formation of hydrogen bonds. "Complementary," as used herein, also refers to sequence complementarity between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

The term "biomolecule" refers to any molecule that is can be found in a biological sample. These are preferably peptides, proteins, sugars as oligosaccharides, lipids, steroids, prostaglandins, prostacyclines, and nucleic acids (including DNA and RNA). The term "biological sample" refers to any solid or fluid sample obtained from microorganisms, viruses and multicellular organisms as plants, animals and human beings, particularly human patients affected with a disease. Examples are biological fluids as blood, plasma, serum, urine, bile, cerebrospinal fluid, or any bodily secretion. A "biological sample" can also be a sample obtained from an organ or tissue, preferably a biopsy, and comprises cells. The term "target biomolecule" should denote a "biomolecule" in a sample which should be analyzed and is the target (of analysis), i.e. the presence, non-presence or amount thereof in a sample should be determined. For example, if it has to be determined whether blood contains the human immunodeficiency virus, the "target biomolecule" may be a biomolecule of the human immunodeficiency virus or more specifically a protein of this virus that can be recognized by antibodies in an immunological test and that has an amino acid sequence specific for the virus in question.

The plural abreviation "spp." is used to refer to all the individual species within a genus, e.g., Cornus spp. refers to all the plants within the dogwood genus. Species is a fundamental category of taxonomic classification that ranks below a genus and above subspecies, a population or series of populations whose individuals have the potential to freely breed with one another and that is discontinuous in variation from other populations or series of populations.

DESCRIPTION OF THE FIGURES

All figures show the temperature on the x-axis and the negative first derivative (−dF/dT Fluorescence) of the fluorescence intensity graph on the y-axis.

DETAILED DESCRIPTION OF THE INVENTION

Figure 1:
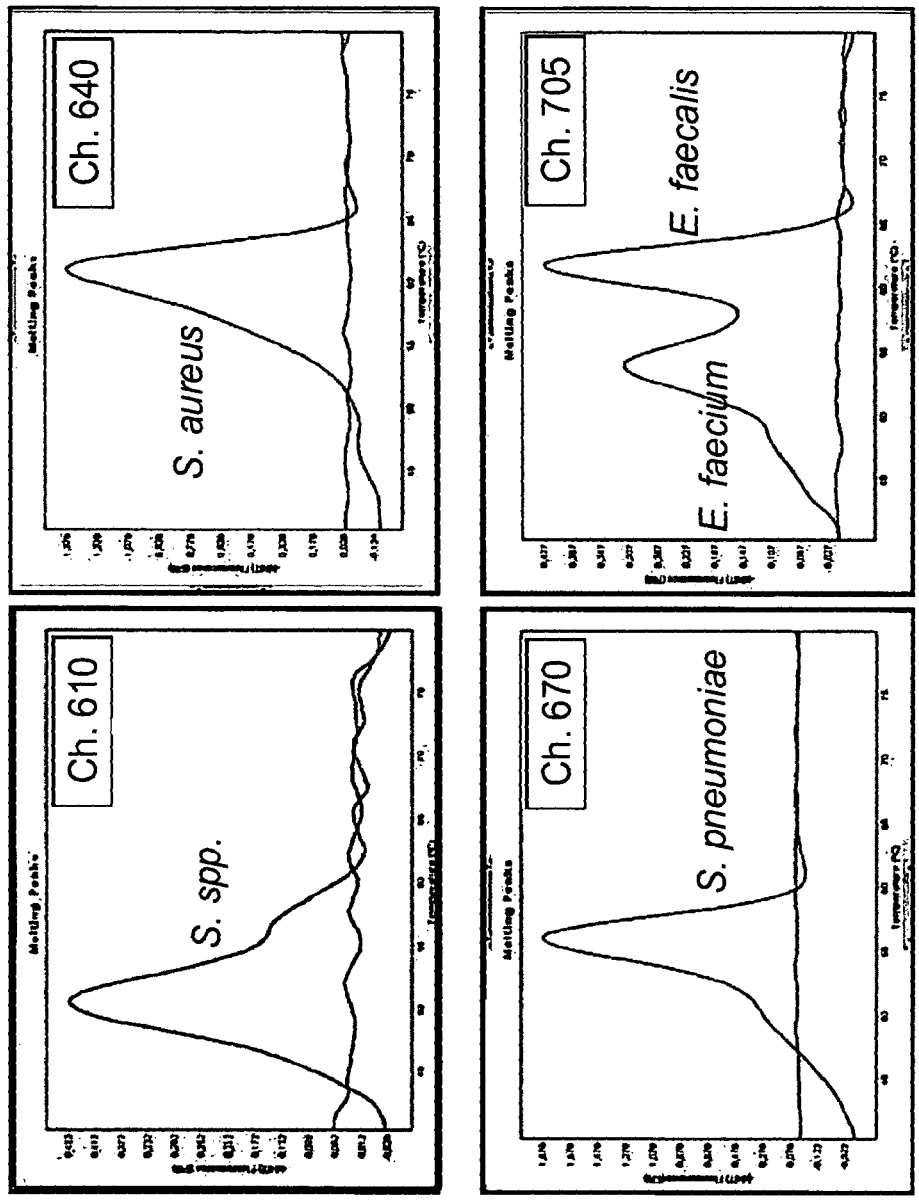
FIG. 1 shows the result of a melting curve analysis for RC G+ (Reaction Control G+). For each of the different target organisms represented in the RC G+ reagent, individual melting curve peaks (dF/dT; F=fluorescense; T=temperature) could be detected in the different detection channels and at different melting peak temperatures.
Figure 2:
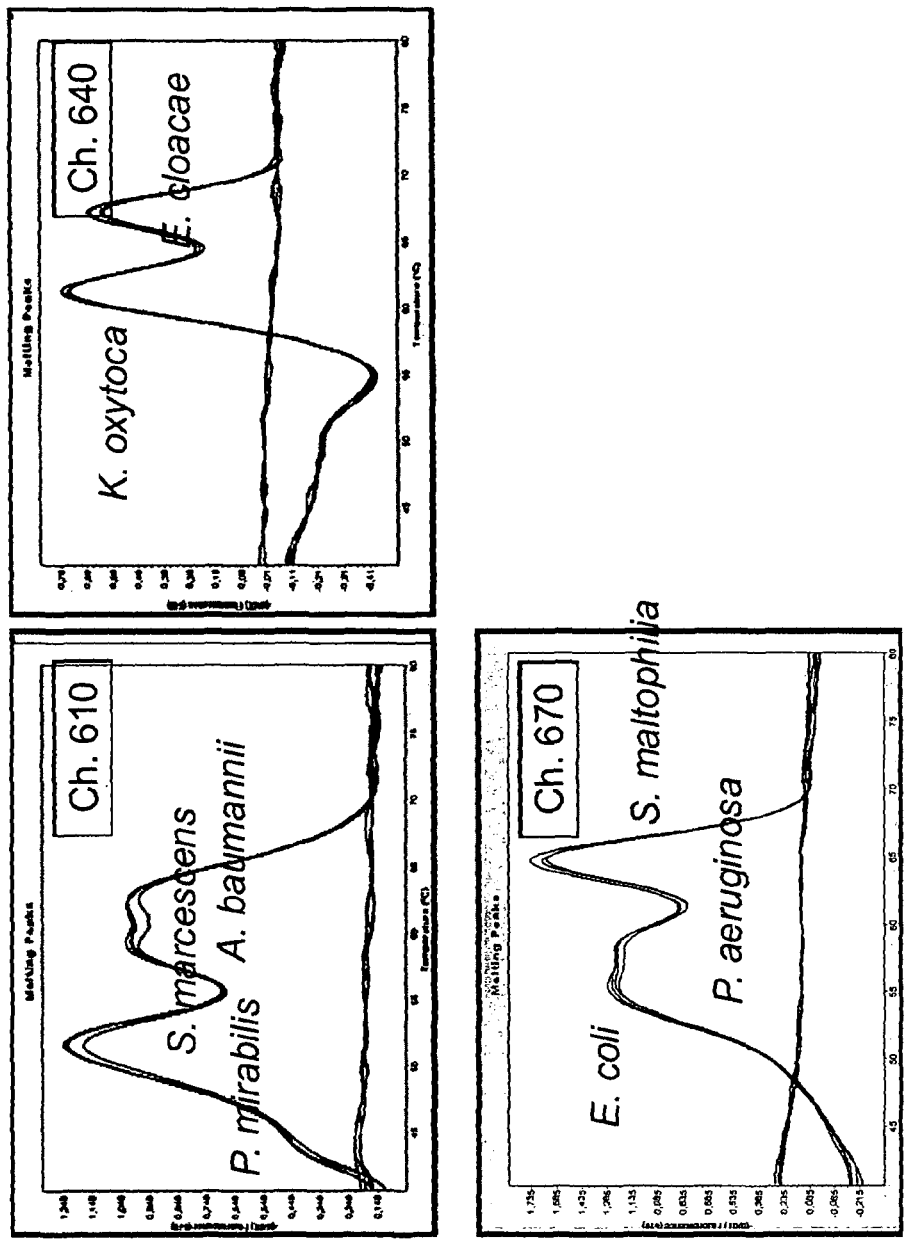
FIG. 2 shows the result of a melting curve analysis for RC G− (Reaction Control G−). For each of the different target organisms represented in the RC G− reagent, individual melting curve peaks (dF/dT; F=fluorescense; T=temperature) could be detected in the different detection channels and at different melting peak temperatures.
Figure 3:
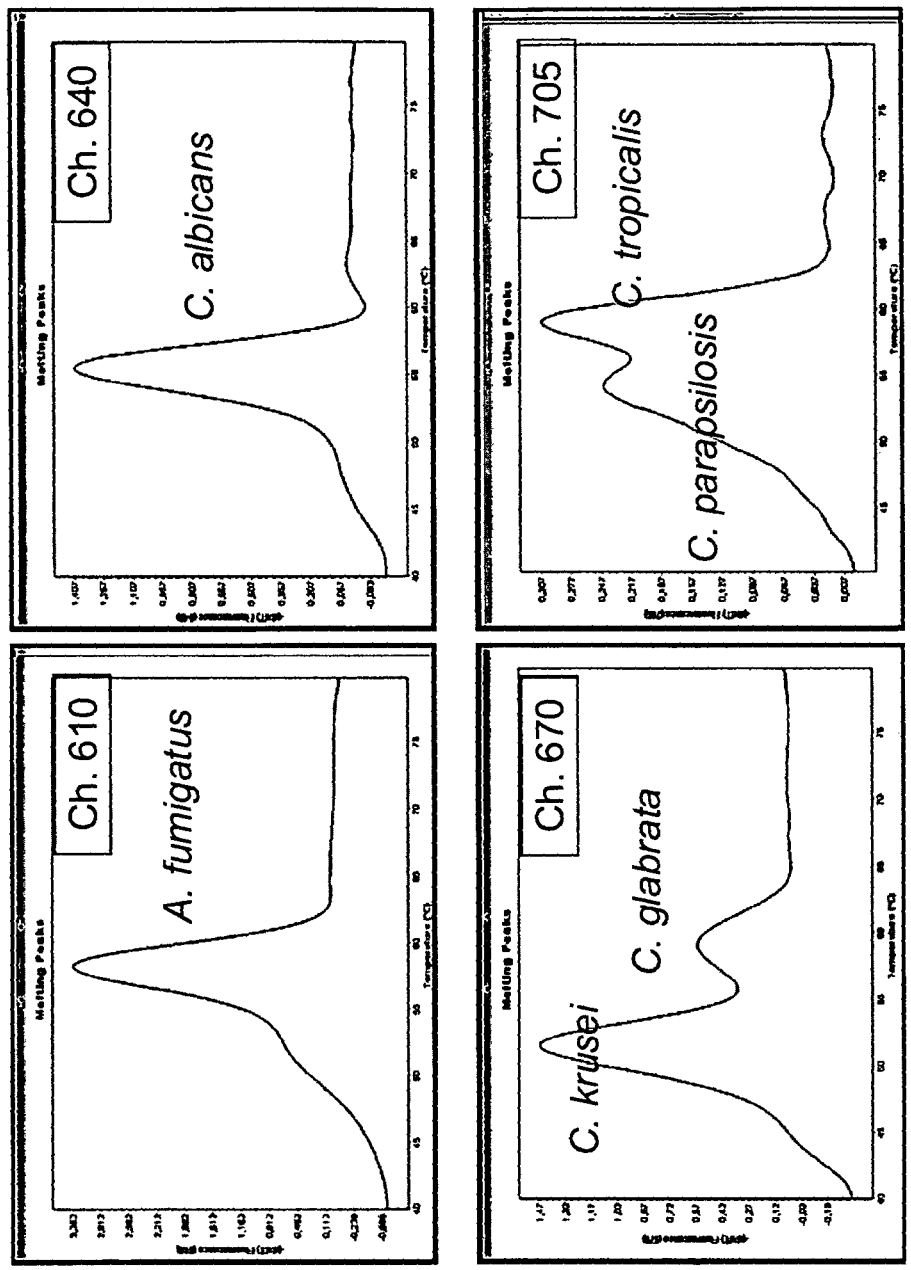
FIG. 3 shows the result of a melting curve analysis for RC F (Reaction Control F). For each of the different target organisms represented in the RC F reagent, individual melting curve peaks (dF/dT; F=fluorescense; T=temperature) could be detected in the different detection channels and at different melting peak temperatures.
Figure 4:
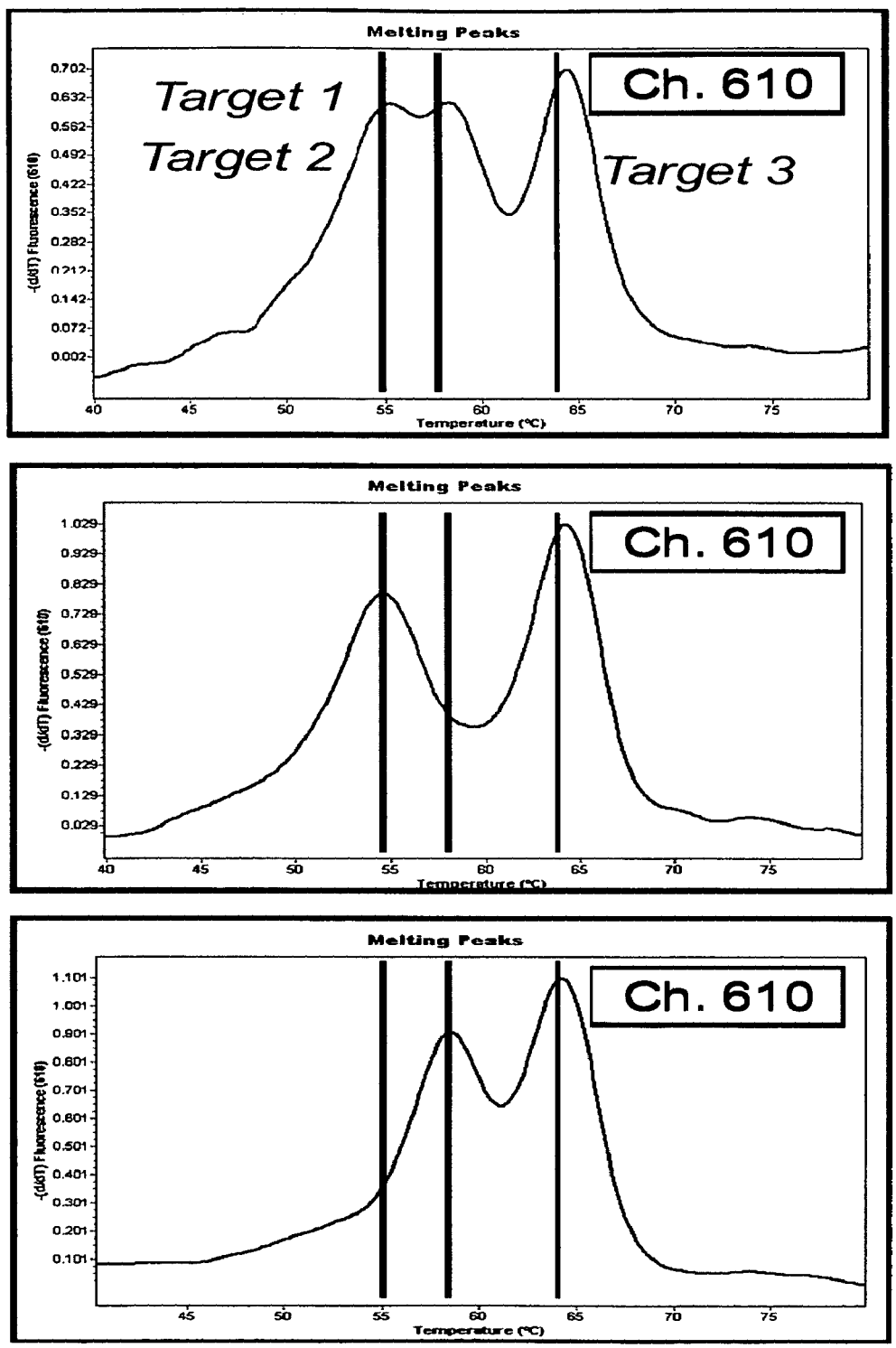
FIG. 4 shows the melting curve analysis for RC G− (Reaction Control G−; detection channel 610) obtained in 3 different multiplex experiments. In the first experiment melting peaks (dF/dT; F=fluorescense; T=temperature) for all 3 target organisms represented in the RC G− were obtained, whereas in the second and third experiment the melting peak for target 2 and target 1 respectively is missing. The missing melting curve peaks clearly indicate a failure of the reagents and/or unsuitable reaction conditions used in experiment 2 and 3 for the detection of target 2 and target 1 respectively.
Figure 5:
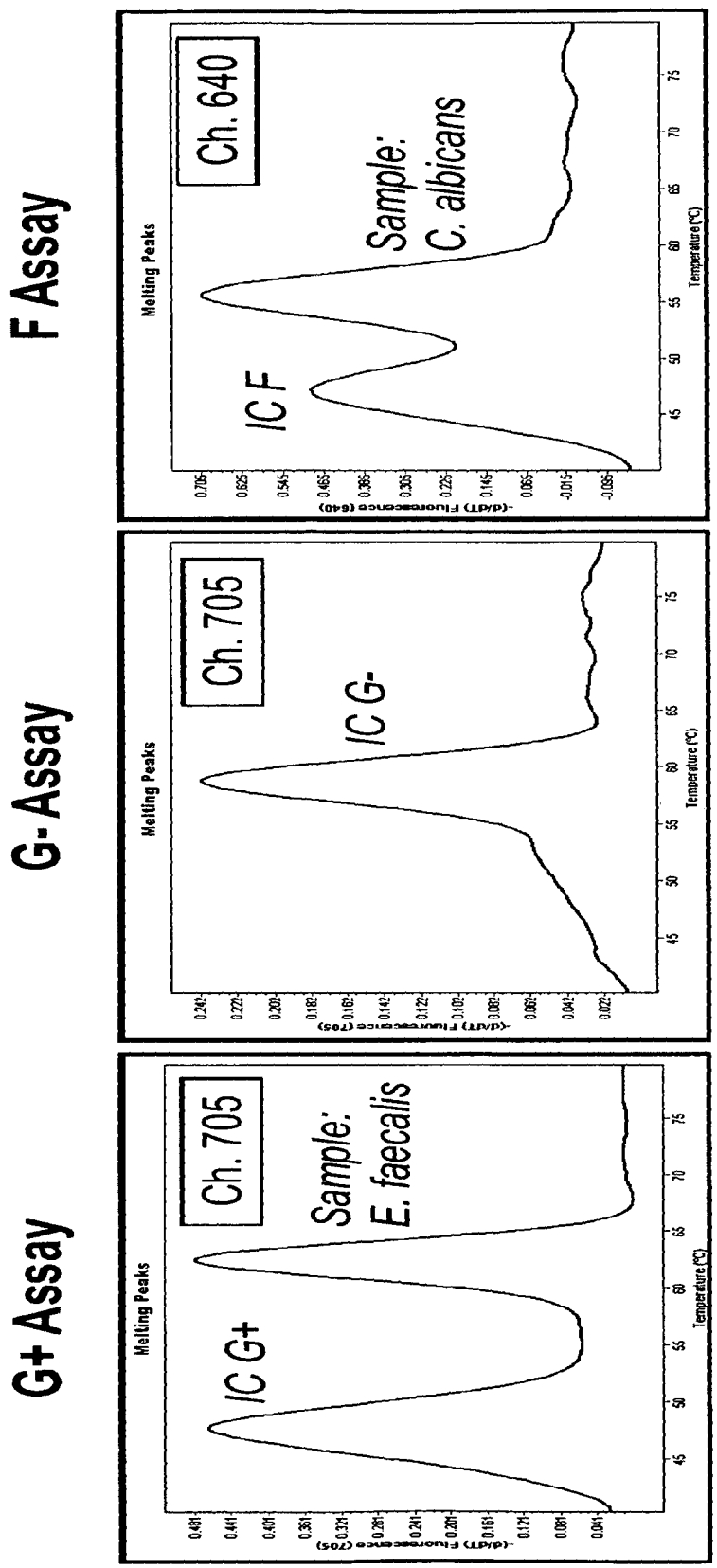
FIG. 5 shows the result of a melting curve analysis for blood samples containing E. faecalis and C. albicans. IC (internal control) was spiked to the blood samples before sample preparation and co-purified together with the target nucleic acid. Individual melting curve signals were obtained for 2 target organisms (E. faecalis, C. albicans) in the G+ assay and F assay, but not in the G− assay. However for all 3 assays (G+, G−, F) the corresponding IC signal was detected at the expected melting peak temperature (IC G+, IC G−, IC F). The IC signals observed indicate suitable reaction conditions used and therefore demonstrate the validity of the results obtained for all 3 assays.

Conventional techniques of molecular biology and nucleic acid chemistry, which are within the skill of the art, are explained in the literature. See, for example, Sambrook, J., et al., Molecular Cloning: A Laboratory Manual, Cold Spring Harbor Laboratory Press, Cold Spring Harbor, N.Y., 1989; Gait, M. J., Oligonudeotide Synthesis, a practical approach, ed. 1984, IRL Press, Oxford, England; Hames, B. D., and Higgins, S. J., Nucleic Acid Hybridisation, a practial approach, ed. 1985, IRL Press, Oxford, England; and a series, Methods in Enzymology, Academic Press, Inc., all of which are incorporated herein by reference. All patents, patent applications, and publications mentioned herein, both supra and infra, are incorporated herein by reference.

In an embodiment of the invention, a method is provided for detecting the presence or the absence of a target biomolecule in a sample suspected to comprise the target biomolecule comprising:
a) either
a1) adding an internal control biomolecule
to the sample suspected to comprise the target biomolecule,
to a negative control sample not comprising the target biomolecule,
to a positive control sample comprising the target biomolecule, and
to a reagent control sample comprising the target biomolecule
a2) adding an internal control biomolecule
to the sample suspected to comprise the target biomolecule,
to a negative control sample not comprising the target biomolecule, and
to a positive control sample comprising the target biomolecule, and providing a reagent control sample comprising the target biomolecule, b) optionally purifying the biomolecules from the samples of step a) to obtain samples comprising the purified biomolecules,
c) determining in each sample obtained in step a) or b) the presence or the absence of a signal of the internal control biomolecule and of the target biomolecule,
d) verifying the presence or absence of the signal of the target biomolecule in the sample suspected to comprise the target biomolecule by:
checking the sample suspected to comprise the target biomolecule for the presence of a signal for the target biomolecule independently from the presence of a signal of the internal control biomolecule or checking for the presence of a signal of the internal control biomolecule in the case of an absence of a signal for the target biomolecule,
checking the negative control sample for the presence of a signal of the internal control biomolecule and for the absence of a signal of the target biomolecule,
checking the positive control sample for the presence of a signal of the target biomolecule and for the presence of a signal of the internal control biomolecule, and
checking the reagent control sample for the presence of a signal for the target biomolecule in step d) of the method or checking the reagent control sample for the presence of a signal for the target biomolecule and optionally for the internal control biomolecule,
e) detecting the presence or the absence of the target biomolecule whereby the presence or absence of the signals for the target biomolecule and the internal control biomolecule determined in step c) and verified in step d) indicate the presence or the absence of the target biomolecule in the test sample.

The method according to the invention makes use of various controls that allow to verify whether all steps of the reaction worked properly and whether the signal obtained can be trusted and can be reliably used for detecting the presence or the absence of a target biomolecule in a sample. For example, the use of two positive controls, i.e. the positive control and the reagent control according to the invention, preferably introduced in different steps of the process, preferably before and after purification of the biomolecules, will allow checking which steps of the method, in particular the purification of the biomolecules, may not work properly and what the origin of errors may be. By using an internal control in the negative control sample, the absence of the signal of the target biomolecule in the negative control sample can be checked whether it results from a correct absence of the target biomolecule or an inadvertent introduction of an inhibitory substance into the negative control sample. By using an internal control in the positive control sample and the reagent control sample, the potential and inadvertent absence of the signal of the target biomolecule in these samples can be checked whether it results from an inadvertent introduction of an inhibitory substance into these samples. In summary, the method according to the invention allows the check and the verification of various steps in a method for detecting the presence or the absence of a target biomolecule in a sample suspected to comprise the target biomolecule. This is particularly advantageous for multiplex assays, in particular in connection with melting curve analysis in the case of nucleic acids which allows the additional separation of signals arising from different target nucleic acids.

The internal control biomolecule (or control biomolecule or biomolecule) is an internal standard to serve as a control for the detection of the target biomolecule. The use of the internal control permits the control of the purification, signal determination and detection thus allowing the monitoring of assay performance and even quantification of the target biomolecule. It is added to the test sample and other samples to control the reactions made therewith and shall allow to detect the presence of inhibitors of the reactions. As the internal control biomolecule is also present in the samples comprising the target biomolecule and is expected to provide a signal, the internal control biomolecule or the signal thereof has to be differentiable from the target biomolecule and/or the signal thereof.

For that purpose, in one embodiment of the invention, the internal control biomolecule comprises a part of the target biomolecule. The internal control biomolecule may also comprise a part of the target biomolcule and a part that it not a part of the target biomolecule. The internal control biomolecule or the part of the internal control biomolecule that is not a part of the target biomolecule may be very similar to the target biomolecule, i.e. should have similar biomolecular properties as the target biomoleucles. This means that if the target biomolecule is a protein, the internal control biomolecule should be a protein with a similar amino acid sequence to the target protein, i.e. should have preferentially an amino acid sequence that is 60% or 80% identical to the amino acid sequence of the target protein and should thus have similar molecular properties, i.e. should behave similar to the target biomolecule or protein but should still yield a signal different to the target biomolecule. Then a different antigenic site should allow the creation of a different signal compared to the target protein.

In certain embodiments of the invention, the internal control biomolecule may be a mixture or a group of internal control biomolecules, i.e. more than one internal control biomolecule. The internal control biomolecule or mixtures thereof are normally provided in a solution comprising a buffer and a salt, i.e. in the form of a sample. Hence, a sample comprising an internal control nucleic acid is added to the respective other sample according to the invention.

In the case of a nucleic acid as the target biomolecule, the internal control nucleic acid includes a nucleic acid sequence that differs from the target nucleic acid sequence but may be similar thereto, is capable of hybridizing with a sequence specific probe and is capable of amplification. Therefor, the internal control nucleic acid derived amplicon has a similar length and contents of G and C bases as the target nucleic acid and may comprise a unique probe binding site. Therefor, the internal control nudeic acid should be a nucleic acid with a similar nucleic acid sequence to the target nucleic acid, i.e. should have a nucleic acid sequence that is 60% or 80% identical to the nucleic acid sequence of the target nucleic acid and should thus have similar molecular properties. The internal control nucleic acid is usually a nucleic acid cloned into a plasmid and comprising a part of the target nucleic acid and a part that is not a part of the target nucleic acid, i.e. a part that is used for the detection of the target nucleic acid and that can be used for the differentiation of the signal of the internal control nucleic acid and the signal of the target nucleic acid. In other embodiments, the internal control nucleic acid contains the same primer binding sites as the target nucleic acid, i.e. the same primers can be used for the amplification of the target nucleic acid and the internal control nucleic acid, and the internal control nucleic acid has probe binding site that has a different nucleic acid sequence as the probe binding site of the target nucleic acid thus allowing differentiation. Preferably, according to the invention, the internal control nucleic acid is a mixture or a group of internal control nucleic acids, i.e. more than one internal control nucleic acid. The internal control nucleic acid or mixtures thereof are normally provided in a solution comprising a buffer and a salt. Hence, a sample comprising an internal control nucleic acid is added to another sample. The solution comprising the internal control nucleic acid is free of contaminating target nucleic acid and provides the internal control nucleic acids at low concentration to allow monitoring of the inhibition of the PCR amplification. Details about the construction and the general methodology to use internal control nucleic acids can be found e.g. in EP 1 236 805, WO 02/18635, Gilliland, G., et al., Proc. Natl. Acad. Sci. USA 87 (1990) 2725-2729 and the references described therein and supra.

The sample suspected to comprise the target biomolecule can also be called test sample and is the sample to be tested. Besides the target biomolecule, it may comprise further biomolecules besides the target biomolecule. These further biomolecules are those that are typically present in a biological sample and are those known to an expert skilled in the art, e.g. peptides, proteins, sugars as oligosaccharides, lipids, steroids, prostaglandins, prostacyclines, and nucleic acids (including DNA and RNA). The biological sample refers to any solid or fluid sample obtained from microorganisms, viruses and multicellular organisms, particularly human patients affected with a disease. Examples are biological fluids as blood, plasma, serum, urine, bile, cerebrospinal fluid, or any bodily secretion. A biological sample can also be a sample obtained from an organ or tissue, preferably a biopsy, and comprises cells.

The negative control sample is a sample not comprising the target biomolecule. It may however comprise further biomolecules but not the target biomolecule. These further biomolecules are those described above. In some embodiments, the negative control sample is a solution comprising a salt and a buffer substance (and does not comprise the target biomolecule).

The positive control sample is a sample that comprises the target biomolecule, i.e. it should serve as a positive control which means that it should provide the same signal as the test sample if it contains the target biomolecule. The positive control sample may be a solution comprising the target biomolecule or a part thereof. Preferably the sample is a sample that is treated in the same manner as the test sample, i.e. purification steps for obtaining the target biomolecule contained therein. In the case of a nucleic acid as target biomolecule, the positive control sample is processed through the complete workflow including lysis and nucleic acid isolation as the purification steps and (PCR) amplification and detection. Therefore, the positive control sample is a sample that contains the target biomolecule in the same environment as the test sample. Often the target biomolecule is a biomolecule contained in a virus, a cell or a microorganism, preferentially a nucleic acid. Then the test sample as well as the positive control sample may comprise a virus, a cell or a microorganism comprising the target biomolecule. The positive control sample may comprise a microorganism obtained from a positive blood culture that is spiked into a negative human blood matrix. Therefore, the positive control sample is a sample that may comprise a virus, a cell or a microorganism that comprises the target biomolecule and whereby the sample further comprises the same or nearly the same further biomolecules (i.e. environment) that the sample suspected to comprise the target biomolecules contains. If the target biomolecule is a group of target biomolecules, each of the target bioelcules is contained in a respective virus, cell or microorganism. Then the positive control sample may contain one or more or all members of the group of target biomolecules as it is sufficient to see that the sample treatment worked at least for one of them. This is of particular importance if the viruses, cells or microorganisms are pathogenic as not positive control sample comprising a complete mixture of different, pathogenic and maybe of different disease-causing potential possessing viruses, cells, or microorganisms has to be sold and delivered to a customer. Therefore, the positive control sample may only comprise one target biomolecule in the case of a group of target biomolecules to be tested for.

The reagent control sample is also a positive control sample, i.e. it should serve as a positive control which means that it should provide the same signal as the test sample if it contains the target biomolecule. The reagent control sample may be a solution comprising the target biomolecule or a part thereof. However, it is a positive control that is not treated in the absolutely same manner as the test sample as the positive control sample, i.e. there are e.g. no purification steps for obtaining the target biomolecule contained therein. In the case of a nucleic acid as target biomolecule, the positive control sample is processed through the complete workflow including lysis and nucleic acid isolation as the purification steps and (PCR) amplification and detection but the reagent control sample only undergoes (PCR) amplification and detection. Therefore, the positive control sample may be a sample that contains the target biomolecule in the same environment as the test sample but often this is not the case. Often the target biomolecule is a biomolecule contained in a virus, a cell or a microorganism, preferentially a nucleic acid. Then the test sample as well as the positive control sample may comprise a virus, a cell or a microorganism comprising the target biomolecule but the reagent control sample only comprises the target biomolecule. Therefore, the reagent control sample may be a sample that comprises the target biomolecule that is not contained in a virus, a cell or a microorganism and whereby the sample may or may not further comprise other biomolecules. In the case of a nucleic acid as the target biomolecule, the target nucleic acid may be linked or connected to other nucleic acids as it is the case for example in a plasmid where the nucleic acid to be amplified, the amplicon, is cloned into a plasmid that allows the propagation of this target nucleic acid. If the target biomolecule is a group of target biomolecules, each of the target biomolecules is contained in the reagent control sample, i.e. in the case of a group of target nucleic acids, e.g. for the detection of various viruses or microorganisms, the reagent control sample may comprise the group of target nucleic acids, i.e. a group of plasmids comprising the group of target nucleic acids. The reagent control sample may comprise in the case of a group of target nucleic acids a mixture of individual cloned target nucleic acid sequences covering the amplified region of each hybridization probe pair used.

According to the invention, the internal control biomolecule may be added or contained within the reagent control sample. The samples can be checked for the presence of the respective signals by methods know to the expert skilled in the art. The sample suspected to comprise the target biomolecule is checked for the presence of a signal for the target biomolecule independently from the presence of a signal of the internal control biomolecule or checked for the presence of a signal of the internal control biomolecule in the case of an absence of a signal for the target biomolecule. In the case of a nucleic acid and the presence of a signal for the target nucleic acid there is not necessarily a signal of the internal control nucleic acid present as the same primers are used for amplification and the target nucleic acid may be present in higher amounts not allowing the amplification and detection of the internal control nucleic acid.

In another embodiment of the invention, the biomolecules or the nucleic acids are purified from the samples using e.g.

solid phases and methods known to the expert in the field. The samples may comprise cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. In certain embodiments of the invention the sample is a fluid from the human or animal body, e.g., the sample is blood, blood plasma, blood serum or urine. The blood plasma may comprise EDTA-, heparin- or citrate-treated blood plasma. The biological sample comprising the nucleic acids is lysed to create a mixture of biological compounds comprising nucleic acids and other components. Procedures for lysing samples are known by the expert and can be chemical, enzymatic or physical in nature. A combination of these procedures is applicable as well. For instance, lysis can be performed using ultrasound, high pressure, shear forces, alkali, detergents or chaotropic saline solutions, or proteases or lipases. For the lysis procedure to obtain nucleic acids, special reference is made to Sambrook et al.: Molecular Cloning, A Laboratory Manual, 2nd Edition, Cold Spring Harbour Laboratory Press, Cold Spring Harbour, N.Y. and Ausubel, F., et al.: Current Protocols in Molecular Biology 1987, J. Wiley and Sons, NY. Then the nucleic acids are isolated from the lysis mixture using the methods and solid phases according to the invention and can then be subjected to the methods according to the invention. Chaotropic agents are also used to lyse cells to prepare a mixture between nucleic acids and other biological substances (see e.g. Sambrook, J., et al., Molecular Cloning: A Laboratory Manual, 2nd Edition, Cold Spring Harbor Laboratory Press, Cold Spring Harbor, N.Y., 1989, or EP 0 389 063). Afterwards material comprising glass or silica is added and a purification effect results from the behavior of DNA or RNA to bind to material with a glass surface under these conditions i.e. in the presence of certain concentrations of a chaotropic agent, higher concentrations of organic solvents or under acidic conditions. Magnetic glass particles as described in WO 01/37291 can be used as well.

In yet another embodiment, the target biomolecule is a group of target biomolecules.

In still another embodiment, the biomolecule is a nucleic acid.

In yet another embodiment, the target nucleic acid and the internal control nucleic acid is amplified before step c). In certain embodiments of the invention, the nucleic acids are amplified with the polymerase chain reaction (PCR; EP 0 201 184, EP 0 200 362, U.S. Pat. No. 4,683,202). The amplification method may also be the Ligase Chain Reaction (LCR, Wu, D. Y., and Wallace, R. B., Genomics 4 (1989) 560-9 and Barany, F., Proc Natl Acad Sci USA 88 (1991) 189-93; Polymerase Ligase Chain Reaction (Barany, F., PCR Methods Appl 1 (1991) 5-16); Gap-LCR (PCT Patent Publication No. WO 90/01069); Repair Chain Reaction (European Patent Publication No. EP 0 439 182 A2), 3SR (Kwoh, D. Y., et al., Proc Natl Acad Sci USA 86 (1989) 1173-7; Guatelli, J. C., et al., Proc Natl Acad Sci USA 87 (1990) 1874-8; PCT Patent Publication No. WO 92/08808), and NASBA (U.S. Pat. No. 5,130,238). Further, there are strand displacement amplification (SDA), transcription mediated amplification (TMA), and Qβ-replicase amplification (for a review see e.g. Whelen, A. C., and Persing, D. H., Annu Rev Microbiol 50 (1996) 349-73; Abramson, R. D., and Myers, T. W., Curr Opin Biotechnol 4 (1993) 41-7).

In another embodiment, the method comprises the step of detecting the amplified nucleic acid. The amplified nucleic acid may be determined or detected by standard analytical methods known to the person skilled in the art and described e.g. in Sambrook, et al., Molecular Cloning, Cold Spring Harbor University Press (1989); Lottspeich and Zorbas, Bioanalytik (1998), Eds. L. a. Zorbas, Spektrum Akademische Verlag, Heidelberg, Berlin, Germany, or in Ausubel, F., et al., in "Current Protocols in Molecular Biology" (1994), Eds. F. Ausubel, R. Brent and K. R. E., Wiley & Sons Verlag, N.Y. There may be also further purification steps before the target nucleic acid is detected e.g. a precipitation step. The detection methods may include but are not limited to the binding or intercalating of specific dyes as ethidium bromide which intercalates into the double-stranded DNA and changes its fluorescence thereafter. The purified nucleic acids may also be separated by electrophoretic methods optionally after a restriction digest and visualized thereafter. There are also probe-based assays which exploit the oligonucleotide hybridisation to specific sequences and subsequent detection of the hybrid. It is also possible to sequence the target nucleic acid after further steps known to the expert in the field. Other methods apply a plurality of nucleic acid sequences to a silicon chip to which specific probes are bound and yield a signal when a complementary sequences bind.

In certain embodiments of the invention, the nucleic acid is detected by measuring the intensity of fluorescence light as fluorescence signal during amplification. This method entails the monitoring of real time fluorescence. Therefore, in another embodiment, the signal of the target nucleic acid or of the internal control nucleic acid is a fluorescent signal. The fluorescent signal may be generated by a label attached to a probe that hybridizes to the target nucleic acid or the internal control nucleic acid.

One embodiment exploiting simultaneous amplification and detection by measuring the intensity of fluorescent light is the method performed in the COBAS TaqMan® instrument as disclosed in WO 92/02638 and the corresponding US patents U.S. Pat. No. 5,210,015, U.S. Pat. No. 5,804,375, U.S. Pat. No. 5,487,972. This method exploits the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments. The signal generated by the hydrolysis of the labeled oligonucleotide is detected and/or measured. The format used in the TaqMan® instrument eliminates the need for a solid phase bound reaction complex to be formed and made detectable. In more general terms, the amplification and/or detection reaction of the method according to the invention is a homogeneous solution-phase assay.

Other embodiments are the formats used in the LightCycler® instrument (see e.g. U.S. Pat. No. 6,174,670). These formats apply the fluorescent resonance energy transfer technology (see, for example, U.S. Pat. Nos. 4,996,143, 5,565,322, 5,849,489, and 6,162,603) and are based on the fact that when a donor and a corresponding acceptor fluorescent label are positioned within a certain distance of each other, energy transfer takes place between the two fluorescent labels that can be visualized or otherwise detected and/or quantitated. As used herein, two probes, each containing a fluorescent label can hybridize to an amplification product at particular positions determined by the complementarity of the probes to the target nucleic acid. The fluorescent label according to the invention of the probe may be a donor or acceptor fluorescent label. Upon hybridization of the probes to the amplification product at the appropriate positions, a FRET signal is generated. Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range. As used herein with respect to donor and corresponding acceptor fluorescent labels, "corresponding" refers to an acceptor fluorescent label having an excitation spectrum that overlaps the emission spectrum of the donor fluorescent label. Accordingly, efficient non-radiative energy transfer can be produced there between. The fluorescent label may be e.g. fluorescein as the donor fluorescent label, whereby the acceptor fluorescent label is rhodamine. Other labels may comprise cyanine dyes or labels, e.g., Cy5 or Cy5.5 as described in U.S. Pat. No. 6,174,670. Therefore, the fluorescent signal may be generated by a pair of probes hybridizing to the respective nucleic acid wherein the members of said pair of probes hybridize to the respective nucleic acid within no more than five nucleotides distance to one another, wherein the first probe of said pair of probes is labeled with a donor fluorescent label and wherein the second probe of said pair of probes is labeled with a corresponding acceptor fluorescent label and wherein the hybridization of the first and second probe to the respective nucleic acid brings them into in a resonance energy transfer relationship.

In some embodiments of the invention, step c) of the method according to the invention comprises the following substeps c1) adding to the samples obtained in step a) or b)
  a pair of primers hybridizing to the internal control nucleic acid and the target nucleic acid or two pairs of primers the first one hybridizing to the internal control nucleic acid and the second one hybridizing to the target nucleic acid,
  a first pair of probes hybridizing to the internal control nucleic acid wherein the members of said first pair of probes hybridize to the internal control nucleic acid with no more than five nucleotides between the probes, wherein the first probe of said first pair of probes is labeled with a first donor fluorescent label and wherein the second probe of said first pair of probes is labeled with a first acceptor fluorescent label and wherein the hybridization of the first and second probe to the internal control nucleic acid brings them into in a resonance energy transfer relationship;
  a second pair of probes hybridizing to the target nucleic acid wherein the members of the second pair of probes hybridize to the target nucleic acid with no more than five nucleotides between the probes, wherein the first probe of said second pair of probes is labeled with a second donor fluorescent label and wherein the second probe of said second pair of probes is labeled with a second acceptor fluorescent label and wherein the hybridization of the first and second probe to the target nucleic acid brings them into in a resonance energy transfer relationship; and
  a thermostable nucleic acid polymerase and reagents necessary for amplifying the internal control nucleic acid and the target nucleic acid, c2) amplifying in the samples the internal control nucleic acid and the target nucleic acid if present in the respective sample, c3) determining in each sample separately the presence or absence of a fluorescent signal of the internal control nucleic acid and of the target nucleic acid as a function of the temperature of the respective sample,
  whereby the fluorescent signal specific for the internal control nucleic acid is generated by fluorescence resonance energy transfer between the first donor fluorescent label of said first probe of the first pair of probes and the first acceptor fluorescent label of the second probe of the first pair of probes, and
  whereby the fluorescence signal specific for the target nucleic acid is generated by fluorescence resonance energy transfer between the first donor fluorescent label of said first probe of the second pair of probes and the first acceptor fluorescent label of the second probe of the second pair of probes.

The presence or absence of a fluorescent signal of the internal control nucleic acid and of the target nucleic acid can be determined as a function of the temperature of the respective sample ("melting curve analysis"). For such an analysis the temperature of the sample is increased continuously and the exact melting temperature is determined at which the previously generated hybridization complex between (amplified) target nucleic acid and hybridization probe is resolved. Such an approach may be even used in order to detect differences in melting temperatures of target molecules which only differ from each other by a single nucleotide polymorphism. In other words, analysis can even be used for the detection or identification of point mutations. Examples of such techniques are disclosed in detail in WO 97/46707, WO 97/46712 and WO 97/46714, the disclosures of which are hereby incorporated by reference.

Several detection formats based on target dependent fluorescent signaling have been disclosed, which enable continuous monitoring of the generation of PCR amplification products or identification of mutations during a subsequent melting curve analysis analysis (reviewed in Wittwer, Carl T., et al., BioTechniques 22 (1997) 130-138). These detection formats include but are not limited to:

1. Increased Fluorescence Resonance Energy Transfer Upon Hybridization

For this detection format, two oligonucleotide hybridization probes each labeled with a fluorescent moiety are used which are capable of hybridizing to adjacent but non overlapping regions of one strand of the amplification product. Preferably, one oligonucleotide is labeled at the 5' end and the second oligonucleotide is labeled at the 3' end. When hybridized to the target DNA, the two fluorescent labels are brought into close contact, such that fluorescence resonance energy transfer between the two fluorescent moieties can take place. As a consequence, the hybridization can be monitored through excitation of the donor moiety and subsequent measurement of fluorescence emission of the second acceptor moiety (WO 97/46714).

In a similar embodiment, only one fluorescently labeled probe is used, which together with one appropriately labeled primer may also serve as a specific FRET pair (Bernard, P. S., et al., Analytical Biochemistry 255 (1998) 101-107).

2. Molecular Beacons

A molecular beacon oligonucleotide is labeled with a fluorescent compound and a quencher compound, which due to the secondary structure of the molecule are in close vicinity to each other. Upon binding to the target DNA, the intramolecular hydrogen bonding is broken, and the fluorescent compound attached at one end of the probe is separated from the quencher compound, which is attached at the opposite end of the probe (Lizardi et al., U.S. Pat. No. 5,118,801).

The melting point temperature is usually determined experimentally by subjecting the sample to a constitutive increase in temperature and continously measuring the dissociation of the hybridization complex into single strands. The dissociation can be detected by a variety of different methods, for example by a shift in UV absorbance, by surface plamon resonance or preferably by means of flourescence. In the latter case, the hybridization probe is usually labeled with a fluorescent label, and the generation of a fluorescent signal somehow depends on the formation of the hybridization complex.

In some embodiments, the assay is performed in a homogeneous detection format, e.g., the target nucleic acid may be amplified prior to melting temperature determination in a typical PCR reaction with suitable amplification primers. A suitable hybridization probe is already present during the amplification reaction. The hybridization probe may carry a fluorescent label which is detectable after appropiate excitation. For example, the hybridization probe may be either a molecular beacon (Lizardi et al., U.S. Pat. No. 5,118,801) or a pair of fluorescently labeled oligonucleotides which together are capable of acting according to the so-called FRET-Hybprobe formate (WO 97/46714). After completion of the PCR-reaction, the temperature of the sample is constitutively increased. Fluorescence can be detected as long as the hybridization probe is bound to the target DNA. However, at the melting temperature, the hybridization probe is released from its target, and the fluorescent signal decreases immediately down to the background level. This decrease can be monitored with an appropriate temperature-time plot, such that an exact temperature value can be determined, at which the temperature decrease is observed.

The target nucleic acid may be a group of target nucleic acids and the pair of probes may be a group of pairs of probes whereby each pair of probes hybridizes to a member of the group of target nucleic acids.

In certain embodiments, the label is a fluorescein dye, a rhodamine dye, a cyanine dye, or a coumarin dye. In other embodiments, the label is fluorescein, LC-Red 610, LC-Red 640, LC-Red 670 or LC-Red 705.

The nucleic acid sequence of the target nucleic acid may be a nucleic acid sequence specific for a microorganism, a cell or a virus. In some embodiments, the microorganism is a gram-positive or a gram-negative microorganism or a fungi, such as
  a) the gram-positive microorganism may be *Proteus mirabilis, Serratia marcescens, Acinetobacter baumannii, Klebsiella pneumoniae, Klebsiella oxytoca, Enterobacter aerogenes, Enterobacter cloacae, Escherichia coli, Pseudomonas aeruginosa,* or *Stenotrophomonas maltophilia,*
  b) the gram-negative microorganism may be a *Staphylococcus* spp., *Enterococcus faecium* or *faecalis* or a *Streptococcus* spp., or
  c) the fungi may be *Candida albicans, Aspergillus fumigatus, Candida krusei, Candida glabrata, Candida parapsilosis,* or *Candida tropicalis.*

In some embodiments of the present invention, the method is automated, i.e. the method carries out an automatable process as e.g. described in WO 99/16781. Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. In some embodiments of the invention, the method may be in a high-throughput format, i.e. the automated methods is carried out in a high-throughput format which means that the methods and the used machine or apparatus are optimized for a high-throughput of samples in a short time.

In another embodiment of the invention, a method for verifying the determination of a signal indicating the presence of a target biomolecule comprising:
  a) providing
    a sample suspected to comprise the target biomolecule and comprising an internal control biomolecule, and
    a negative control sample comprising an internal control biomolecule and not comprising the target biomolecule, and
    a positive control sample comprising the target biomolecule and comprising an internal control biomolecule
    a reagent control sample comprising the target biomolecule and optionally comprising an internal control biomolecule,
  b) determining in each sample the signal of the internal control biomolecule and of the target biomolecule,
  c) verifying the presence of the signal of the target biomolecule in the test sample indicating the presence of the target biomolecule in the test sample by:
    checking the sample suspected to comprise the target biomolecule for the presence of a signal for the target biomolecule independently from the presence of a signal of the internal control biomolecule or checking for the presence of a signal of the internal control biomolecule in the case of an absence of a signal for the target biomolecule,
    checking the negative control sample for the presence of a signal of the internal control biomolecule and for the absence of a signal of the target biomolecule,
    checking the positive control sample for the presence of a signal of the target biomolecule and for the presence of a signal of the internal control biomolecule, and
    checking the reagent control sample for the presence of a signal for the target biomolecule and optionally for the internal control biomolecule.

In another embodiment of the invention, the internal control biomolecule comprises a part of the target biomolecule, the positive control sample comprises a virus, a microorganism or a cell containing the target biomolecule, or wherein the positive control sample is a solution comprising the target biomolecule or a part thereof, or wherein the reagent control sample is a solution comprising the target biomolecule or a part thereof.

The target biomolecule may be a group of target biomolecules.

In another embodiment, the biomolecule may be a nucleic acid.

In certain embodiments, the target nucleic acid and the internal control nucleic acid are amplified before step b). Exemplary amplification steps are described supra.

Exemplary amplification and detection methods are described supra. In still another embodiment, the signal of the target nucleic acid or of the internal control nucleic acid is a fluorescence signal. More preferably, the fluorescence signal is generated by a label attached to a probe that hybridizes to the target nucleic acid or the internal control nucleic acid.

All other embodiments and specific descriptions of embodiments of the method for verifying the determination of a signal indicating the presence of a target biomolecule are those mentioned for the methods according to the invention, i.e. the method for detecting the presence or the absence of a target biomolecule in a sample suspected to comprise the target biomolecule (supra), the method for detecting the presence or the absence of a member of a group of target nucleic acids in a sample suspected to comprise the member of a group of target nucleic acids (infra) and the method or the method for verifying the determination of a signal indicating the presence or the absence of a member of a group of target nucleic acids (infra).

In still another embodiment of the invention, a method for detecting the presence or the absence of a member of a group of target nucleic acids in a sample suspected to comprise the member of a group of target nucleic acids is provided comprising:

a) adding an internal control nucleic acid
to the sample suspected to comprise a member of the group of target nucleic acids, and
to a negative control sample not comprising a member of the group of target nucleic acids, and
to a positive control sample comprising a member of the group of target nucleic acids, b) providing a reagent control sample comprising the group of target nucleic acids and optionally an internal control nucleic acid, c) optionally purifying the nucleic acids from the samples of step a) and/or b) to obtain samples comprising the purified nucleic acids, d) determining in each sample obtained in the steps a) and b) or in the steps b) and c) the presence or absence of a signal of the internal control nucleic acid and of a signal of a member of the group of target nucleic acids, e) verifying the presence or the absence of the signal of the member of the group of target nucleic acids in the sample suspected to comprise a member of the group of target nucleic acids by:
checking the sample suspected to comprise a member of the group of target nucleic acids for the presence of a signal of a member of the group of target nucleic acids independently from the presence of a signal of the internal control nucleic acid or checking for the presence of a signal of the internal control nucleic acid in the case of an absence of a signal of a member of the group of target nucleic acids,
checking the negative control sample for the presence of a signal of the internal control nucleic acid and for the absence of a signal of the target nucleic acid,
checking the reagent control sample for the presence of a signal of each member of the group of target nucleic acids and optionally of the internal control nucleic acid, and
checking the positive control sample for the presence of a signal of a member of the group of target nucleic acids and for the presence of a signal of the internal control nucleic acid, f) detecting the presence or the absence of a member of the group of target nucleic acids whereby the presence and/or the absence of the signals for a member of the group of target nucleic acids and the internal control nucleic acid determined in step d) and verified in step e) indicate the presence or the absence of a member of the group of target nucleic acids in the sample suspected to comprise a member of the group of target nucleic acids.

This method has the advantage that the use of the reagent control sample comprising the group of target nucleic acids and optionally an internal control nucleic acid will allow to determine whether the reagents, i.e. particularly the primers and probes for detecting all respective member of the group of target nucleic acids are working properly in addition to a control by the internal control nucleic acid.

In some embodiments of the invention, the internal control biomolecule comprises a part of the target biomolecule, the positive control sample comprises a virus, a microorganism or a cell containing the target biomolecule or wherein the positive control sample is a solution comprising the target biomolecule or a part thereof, or the reagent control sample is a solution comprising the target biomolecule or a part thereof In other embodiments of the invention, a member of the group of target nucleic acids and the internal control nucleic acid is amplified before step d). Exemplary amplification steps are described supra.

Exemplary amplification and detection methods are described supra. In other embodiments of the invention, the signal of a member of the group of target nucleic acids or of the internal control nucleic acid is a fluorescent signal. The fluorescent signal may be generated by a label attached to a probe that hybridizes to a member of the group of target nucleic acids or the internal control nucleic acid. In another embodiment, the fluorescent signal may be generated by a member of a group of pairs of probes hybridizing to a member of the group of target nucleic acids or of a pair of probes hybridizing to the internal control nucleic acid wherein the members of each member of the group of pairs of probes hybridizing to the member of the group of target nucleic acids or the members of the pair of probes hybridizing to the internal control nucleic acid hybridize to the respective nucleic acid with no more than five between the probes, wherein the first probe of a pair of probes is labeled with a donor fluorescent label and wherein the second probe of a pair of probes is labeled with a corresponding acceptor fluorescent label and wherein the hybridization of the first and second probe to the member of the group of target nucleic acids or the internal control nucleic acid brings them into a resonance energy transfer relationship.

Step d) of the method according to the invention may comprise the following substeps d1) adding to the samples obtained in step a) and b) or steps b) and c)
a pair of primers hybridizing to the internal control nucleic acid and to a member of the group of target nucleic acids or a pair of primers hybridizing to the internal control nucleic acid and a group of of pairs of primer each member thereof hybridizing to a member of the group of target nucleic acids,
a first pair of probes hybridizing to the internal control nucleic acid wherein the members of said first pair of probes hybridize to the internal control nucleic acid with no more than five nucleotides between the probes, wherein the first probe of said first pair of probes is labeled with a first donor fluorescent label and wherein the second probe of said first pair of probes is labeled with a first acceptor fluorescent label and wherein the hybridization of the first and second probe to the internal control nucleic acid brings them into in a resonance energy transfer relationship;

a group of pairs of probes each member hybridizing to a member of the group of target nucleic acids wherein the members of the group of pairs of probes hybridize to the respective member of the group of target nucleic acids with no more than five nucleotides between the probes, wherein the first probe of a member of the group of pairs of probes is labeled with a second donor fluorescent label and wherein the second probe of a member of the group of pairs of probes is labeled with a second acceptor fluorescent label and wherein the hybridization of the first and second probe to the member of the group of target nucleic acids brings them into in a resonance energy transfer relationship; and a thermostable nucleic acid polymerase and reagents necessary for amplifying the internal control nucleic acid and the group of target nucleic acids, d2) amplifying in the samples the internal control nucleic acid and the group of target nucleic acids if present in the respective sample, d3) determining in each sample separately the presence or absence of a fluorescence signal of the internal control nucleic acid and/or of a member of the group of target nucleic acids as a function of the temperature of the respective sample whereby the fluorescence signal specific for the internal control nucleic acid is generated by fluorescence resonance energy transfer between the first donor fluorescent label of said first probe of the first pair of probes and the first acceptor fluorescent label of the second probe of the first pair of probes, and whereby the fluorescence specific for a member of the group of target nucleic acids is generated by fluorescence resonance energy transfer between the first donor fluorescent label of said first probe of the member of the group of pairs of probes and the first acceptor fluorescent label of the second probe of the member of the group of pairs of probes.

The presence or absence of a fluorescent signal of the internal control nucleic acid and/or of a member of the group of target nucleic acids may be determined as a function of the temperature ("melting curve analysis"). The description of the melting curve analysis can be found supra.

The label may be a fluorescein dye, a rhodamine dye, a cyanine dye, or a coumarin dye. IN some embodiments, the label is fluorescein, LC-Red 610, LC-Red 640, LC-Red 670 or LC-Red 705.

In another embodiment of the invention, a member of the group of target nucleic acids comprises a nucleic acid sequence specific for a microorganism, a cell or a virus. The microorganism is a gram-positive or gram-negative microorganism or a fungi, such as, a) the gram-positive microorganism may be *Proteus mirabilis, Serratia marcescens, Acinetobacter baumannii, Klebsiella pneumoniae, Klebsiella oxytoca, Enterobacter aerogenes, Enterobacter cloacae, Escherichia coli, Pseudomonas aeruginosa*, or *Stenotrophomonas maltophilia*, b) the gram-negative microorganism may be a *Staphylococcus* spp., *Enterococcus faecium* or *faecalis* or a *Streptococcus* spp., or c) the fungi may be *Candida albicans, Aspergillus fumigatus, Candida krusei, Candida glabrata, Candida parapsilosis*, or *Candida tropicalis*.

All other embodiments and specific descriptions of embodiments of the method for detecting the presence or the absence of a member of a group of target nucleic acids in a sample suspected to comprise the member of a group of target nucleic acids are those mentioned for the methods according to the invention, i.e. the method for detecting the presence or the absence of a target biomolecule in a sample suspected to comprise the target biomolecule (supra), the method for verifying the determination of a signal indicating the presence of a target biomolecule (supra) and the method for verifying the determination of a signal indicating the presence of a member of a group of target nucleic acids (infra).

In another embodiment of the invention, a method for veriying the determination of a signal indicating the presence of a member of a group of target nucleic acids is provided comprising:

a) providing a sample suspected to comprise a member of the group of target nucleic acids and comprising an internal control nucleic acid, a reagent control sample comprising the group of target nucleic acids and optionally an internal control nucleic acid, a negative control sample not comprising a member of the group of target nucleic acids and comprising an internal control nucleic acid, and a positive control sample comprising a member of the group of target nucleic acids and an internal control nucleic acid, b) determining in each sample the signal of the internal control nucleic acid and of a member of the group of target nucleic acids, c) verifying the presence of the signal of a member of the group of target nucleic acids in the sample suspected to comprise a member of the group of target nucleic acids by:

checking the sample suspected to comprise a member of the group of target nucleic acids for the presence of a signal of a member of the target nucleic acids independently from the presence of a signal of the internal control nucleic acid or checking the sample for the presence of a signal of the internal control nucleic acid in the case of an absence of a signal of a member of the group of target nucleic acids, checking the reagent control sample for the presence of a signal of each member of the group of target nucleic acids, checking the negative control sample for the absence of a signal of a member of the group of target nucleic acids and for the presence of a signal of the internal control nucleic acid, and checking the positive control sample for the presence of a signal of the target biomolecule and for the presence of a signal of the internal control nucleic acid.

In one embodiment, the internal control nucleic acid comprises a part of a member of the group of target nucleic acids, the positive control sample comprises a virus, a microorganism or a cell containing the target nucleic acid or wherein the positive control sample is a solution comprising a member of the group of target nucleic acids or a part thereof, or the reagent control sample is a solution comprising a member of the group of target nucleic acids or a part thereof.

The target nucleic acid and the internal control nucleic acid may be amplified before step c). Exemplary amplification steps are described supra.

Exemplary amplification and detection methods are described supra. In some embodiments, the signal of a member of the group of target nucleic acids or of the internal control nucleic acid is a fluorescent signal. In other embodiments, the fluorescent signal may be generated by a label attached to a probe that hybridizes to a member of the group of target nucleic acids or the internal control nucleic acid.

All other embodiments and specific descriptions of embodiments of the method for verifying the determination of a signal indicating the presence of a member of a group of target nucleic acids are those mentioned for the methods according to the invention, i.e. the method for detecting the presence or the absence of a target biomolecule in a sample suspected to comprise the target biomolecule (supra), the method for verifying the determination of a signal indicating the presence of a target biomolecule (supra) and the method for detecting the presence or the absence of a member of a group of target nucleic acids in a sample suspected to comprise the member of a group of target nucleic acids (supra).

In another embodiment of the invention, a reagent control sample optionally comprising an internal control biomolecule and a positive control sample comprising an internal control biomolecule, both samples comprising the target biomolecule, are used for detecting the presence or the absence of a target biomolecule in a sample suspected to comprise the target biomolecule or for verifying the determination of a signal indicating the presence of a target biomolecule. All embodiments for the method according to the invention also are embodiments of the use according to the invention.

In another embodiment, a kit is provided for the detection of a target nucleic acid or a member of a group of target nucleic acids comprising:
a) a reagent control sample comprising the target nucleic acid or the member of a group of target nucleic acids,
b) a negative control sample not comprising the target nucleic acid or the member of a group of target nucleic acids,
c) a positive control sample comprising the target nucleic acid or the member of the group of target nucleic acids,
d) an internal control nucleic acid, and
e) reagents for detecting the target nucleic acid or the member of a group of target nucleic acids.

In some embodiments, in the kit according to the invention the reagents for detecting the target nucleic acid or the member of the group of target nucleic acids comprise:
a pair of probes and a pair of primers,
a thermostable nucleic acid polymerase, and
reagents for amplifying the target nucleic acid or the member of a group of target nucleic acids.

Such kits known in the art further comprise plasticware which can be used during the sample preparation procedure as e.g. microtitre plates in the 96 or 384 well format or just ordinary reaction tubes manufactured e.g. by Eppendorf (Hamburg, Germany) and all other reagents for carrying out the method according to the invention. Therefore, the kit can additionally contain a material with an affinity to nucleic acids, e.g., a material with a silica surface. In some embodiments, the material with a silica surface is a glass. In some embodiments, the material with an affinity to nucleic acids is a composition comprising magnetic glass particles. The kit can further or additionally comprise a lysis buffer containing e.g. chaotropic agents, detergents or alcohols or mixtures thereof which allows the lysis of cells. These components of the kit according to the invention may be provided separately in tubes or storage containers. Depending on the nature of the components, these may be provided in a single tube or storage container. The kit may further or additionally comprise a washing solution which is suitable for the washing step of the magnetic glass particles when DNA or RNA is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the DNA or RNA bound to the magnetic glass particles. Further, additional reagents or buffered solutions may be present which can be used for the purification process of a nucleic acid, i.e. DNA or RNA.

All other embodiments and specific descriptions of embodiments of the uses and kit according to the invention are those mentioned for the methods according to the invention, i.e. the method for detecting the presence or the absence of a target biomolecule in a sample suspected to comprise the target biomolecule (supra), the method for verifying the determination of a signal indicating the presence of a target biomolecule (supra), the method for detecting the presence or the absence of a member of a group of target nucleic acids in a sample suspected to comprise the member of a group of target nucleic acids (supra) and the method for verifying the determination of a signal indicating the presence of a member of a group of target nucleic acids (supra).

The following examples and figures are provided to aid the understanding of the present invention, the true scope of which is set forth in the appended claims. It is understood that modifications can be made in the procedures set forth without departing from the spirit of the invention.

EXAMPLES

General

All reagents should be checked for contamination by nucleic acids and by the organisms to be detected. Only reagents free of those organisms and the nucleic acids originating therefrom can lead to an optimum sensitivity.

Controls

Mixtures of plasmid DNAs (approx. $10^4$ copies of plasmid DNA) containing the ITS region (ITS: internal transcribed spacer) between the 16s rRNA (ribosomal ribonucleic acid) and the 23sRNA genes (bacterial targets) and between the 18s rRNA and the 28sRNA genes (fungal targets) were used for preparation of RC G−, RC G+, RC F and IC control reagents (RC: reagent control, G−: gram-negative, G+: gram-positive, F: fungi, IC: internal control)

a) RC G−:
pTE-Smar-1: plasmid based on pT3T7BM containing *S. marcescens* 16S/23S-rRNA-spacer region
pTE-Abau-1: plasmid based on pT3T7BM containing *A. baumannii* 16S/23S-rRNA-spacer region
pTE-Koxy-1: plasmid based on pT3T7BM containing *Koxytoca* 16S/23S-rRNA-spacer region
pTE-Eclo-1: plasmid based on pT3T7BM containing *E. cloacae* 16S/23S-rRNA-spacer region
pTE-Ecol-1: plasmid based on pT3T7BM containing *E. coli* 16S/23S-rRNA-spacer region
pTE-Pmir-1: plasmid based on pT3T7BM containing *P. mirabilis* 16S/23S-rRNA-spacer region pTE-Paer-2 plasmid based on pT3T7BM containing *P. aeruginosa* 16S/23S-rRNA-spacer region pTE-Smal-1: plasmid based on pT3T7BM containing *S. maltophilia* 16S/23S-rRNA-spacer region b) RC G+:

pStaph_wt: plasmid based on pT3T7BM containing *S. aureus* 16S/23S-rRNA-spacer region pEntero_1:plasmid based on pT3T7BM containing *E. faecalis* 16S/23S-rRNA-spacer region pEntero_2:plasmid based on pT3T7BM containing *E. faecium* 16S/23S-rRNA-spacer region pStrep_wt plasmid based on pT3T7BM containing *S. pneumoniae* 16S/23S-rRNA-spacer region

RC F:

pAfum-PC-PF1: plasmid based on pT3T7BM containing *A. fumigatus* 18S/28S-rRNA-spacer region pCgla-PC-PF1: plasmid based on pT3T7BM containing *C. glabrata* 18S/28S-rRNA-spacer region pCalb-PC-PF1: plasmid based on pT3T7BM containing *C. albicans* 18S/28S-rRNA-spacer region pCkru-PC-PF1: plasmid based on pT3T7BM containing *C. krusei* 18S/28S-rRNA-spacer region pCtrop-PC-PF1: plasmid based on pT3T7BM containing *C. tropicalis* 18S/28S-rRNA-spacer region pCpara-PC-PF1: plasmid based on pT3T7BM containing *C. parapsilosis* 18S/28S-rRNA-spacer region c) IC:

pTE-Paer-IC/2: plasmid based on pT3T7BM containing *P. aeruginosa* 16S/23S-rRNA-spacer region and IC G--specific probe binding sites pIC G+: plasmid based on pT3T7BM containing *E. faecium* 16S/23S-rRNA-spacer region and IC G+-specific probe binding sites pAfum(FP10/21)-ICv2-PF1:

plasmid based on pT3T7BM containing *C. albicans* 18S/28S-rRNA-spacer region and IC F-specific probe binding sites One suitable vector is pT3T7BM used in the examples which carries a multiple cloning site besides the promoter for the T3 and T7 RNA polymerase and which is available from Roche Diagnostics GmbH (Mannheim, Germany). See Vector database for the sequence (http://seq.yeastgenome.org or http://seq.yeastgenome.org/vectordb/vector_descrip/PT3T7BM.html).

Hardware/Software

A LightCycler® 2.0 instrument (Roche Diagnostics GmbH, Mannheim,. Germany) with 100 µl capillary rotor was used for fluorescence detection of the hybridization probes at 610 nm, 640 nm, 670 nm and 705 nm. Generation of raw data and analysis of data was done using LightCycler software 4.05 (Roche Diagnostics GmbH, Mannheim, Germany).

Reagents

All oligonucleotides mentioned herein were prepared by chemical synthesis. The reagents for attaching labels can be purchased from Roche Diagnostics GmbH (LightCycler Red 640 NHS Ester Cat. No. 2015161; Lightcycler Red 705 Phosphoramidite Cat. No. 2157594; LightCycler Fluorescein (abbreviated 'F' in the following) CPG Cat. No. 3113906). The use of those reagents is described in Biochemica No. 1 (2001), p. 8-13. Cy5-NHS Ester can be obtained from Amersham upon request. LC-Red 610-NHS ester has an emission maximum at 610 nm and was synthesized according to standard protocols using a fluorescent dye as disclosed in U.S. Pat. No. 5,750,409.

FastStart DNA polymerase and FastStart Master were generally used as recommended in the LightCycler® FastStart® DNA Master Hybridization Probes Kit (Roche Diagnostics GmbH Cat. No. 2239272). Following the instructions of the manufacturer of the kit the primers have been used at a final concentrations of 0.3 to 1 µM each and the hybridization probes at a final concentration of approx. 0.2 µM each. The concentration of $MgCl_2$ used was 3.5 mM.

The reagents and kits are available from Roche Diagnostics GmbH (Mannheim, Germany).

Method

Samples (particularly clinical samples) were subjected to a sample preparation in which the nucleic acids were released and purified from the other components of the sample. This was done using MagNA Pure™ LC and MagNA Puree™ LC DNA isolation kit III (bacteria, fungi) (Roche Diagnostics GmbH, Germany, Cat No. 3 264 785). The sample preparation yielded in a specimen containing the nucleic acids in elution buffer.

was processed within the sample preparation (e.g. in the MagNA Pure® instrument) or added to the completed mastermix (see below) dependent on wether it is intended to be an in-process control either for the sample preparation procedure or for assay performance in the LightCycler® instrument in each capillary. With the purified nucleic acid preparations and the corresponding Control reagents (RC G+, RC G--, RC F) as samples a run in the LightCycler® instrument was performed in 100 µl reaction volume using the following thermocyling and melting temperature profile:

|  | Cycles | time (sec) | Temp (° C.) | Slope (° C./s) | Acquisition mode |
|---|---|---|---|---|---|
| Denaturation | 1 | 600 | 95° C. | 20 | None |
| Amplification | 15 | 15 | 95 | 3 | None |
|  |  | 50 | 58 | 20 | None |
|  |  | 40 | 72 | 3 | None |
| Amplification | 30 | 15 | 95 | 3 | None |
|  |  | 50 | 50 | 20 | Single |
|  |  | 40 | 72 | 3 | None |
| Melting curve | 1 | 60 | 95 | 20 | None |
|  |  | 60 | 40 | 20 | None |
|  |  | 0 | 80 | 0.1 | Continuous |
| Cooling | 1 | 30 | 40 | 20 | None |

While the foregoing invention has been described in some detail for purposes of clarity and understanding, it will be dear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for detecting the presence or the absence of a target biomolecule in a sample suspected to comprise the target biomolecule, comprising:

a) adding an internal control biomolecule to the sample suspected to comprise the target biomolecule, and a negative control sample not comprising the target biomolecule, and a positive control sample comprising the target biomolecule, and a second positive control sample comprising the target biomolecule, b) purifying the biomolecules from the samples of step a) except the second positive control sample, to obtain samples comprising the purified biomolecules, c) determining in each sample obtained in step a) or b) the presence or the absence of a signal of the internal control biomolecule and of the target biomolecule, d) verifying the presence or absence of the signal of the target biomolecule in the sample suspected to comprise the target biomolecule by:

checking the sample suspected to comprise the target biomolecule for the presence of a signal for the target biomolecule independently from the presence of a signal of the internal control biomolecule or checking for the presence of a signal of the internal control biomolecule in the case of an absence of a signal for the target biomolecule, checking the negative control sample for the presence of a signal of the internal control biomolecule and for the absence of a signal of the target biomolecule, checking the positive control sample for the presence of a signal of the target biomolecule and for the presence of a signal of the internal control biomolecule, and checking the second positive control sample for the presence of a signal for the target biomolecule in step d) of the method or checking the second positive control sample for the presence of a signal for the target biomolecule and optionally for the internal control biomolecule e) detecting the presence or the absence of the target biomolecule whereby the presence or absence of the signals for the target biomolecule and the internal control biomolecule determined in step c) and verified in step d) indicate the presence or the absence of the target biomolecule in the test sample.

2. The method according to claim 1, wherein the negative control sample is a solution comprising a salt and a buffer substance.

3. The method according to claim 1, wherein the internal control biomolecule comprises a part of the target biomolecule.

4. The method according to claim 1, wherein the second positive control sample and/or the positive control sample is a solution comprising the target biomolecule or a part thereof.

5. The method according to claim 1, wherein the positive control sample comprises a virus, a microorganism or a cell comprising the target biomolecule.

6. The method according to claim 1, wherein the target biomolecule is a group of target biomolecules.

7. The method according to claim 1, wherein the biomolecule is a nucleic acid.

8. The method according to claim 7 wherein the target nucleic acid and the internal control nucleic acid is amplified before step c).

9. The method according to claim 7, wherein the signal of the target nucleic acid or of the internal control nucleic acid is a fluorescent signal.

10. The method according to claim 9, wherein the fluorescent signal is generated by a label attached to a probe that hybridizes to the target nucleic acid or the internal control nucleic acid.

11. The method according to claim 10, wherein the fluorescent signal is generated by a pair of probes hybridizing to the respective nucleic acid wherein the members of said pair of probes hybridize to the respective nucleic acid with no more than five nucleotides between the probes, wherein the first probe of said pair of probes is labeled with a donor fluorescent label and wherein the second probe of said pair of probes is labeled with an acceptor fluorescent label and wherein the hybridization of the first and second probe to the respective nucleic acid brings them into in a resonance energy transfer relationship.

12. The method according to claim 7, wherein the target nucleic acid is a group of target nucleic acids and the pair of probes is a group of pairs of probes, whereby each pair of probes hybridizes to a member of the group of target nucleic acids.

13. The method according to claim 10, wherein the label is a fluorescein dye, a rhodamine dye, a cyanine dye, or a coumarin dye.

14. The method according to claim 7, wherein the nucleic acid sequence of target nucleic acid is a nucleic acid sequence specific for a microorganism, a cell or a virus.

15. The method according to claim 14, wherein the microorganism is a gram-positive or a gram-negative microorganism or a fungi.

* * * * *